US011058385B2

(12) United States Patent
Kunio

(10) Patent No.: US 11,058,385 B2
(45) Date of Patent: Jul. 13, 2021

(54) METHOD FOR EVALUATING CARDIAC MOTION USING AN ANGIOGRAPHY IMAGE

(71) Applicant: CANON U.S.A., INC., Melville, NY (US)

(72) Inventor: Mie Kunio, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 401 days.

(21) Appl. No.: 16/044,931

(22) Filed: Jul. 25, 2018

(65) Prior Publication Data

US 2019/0029623 A1 Jan. 31, 2019

Related U.S. Application Data

(60) Provisional application No. 62/537,204, filed on Jul. 26, 2017, provisional application No. 62/680,780, filed on Jun. 5, 2018.

(51) Int. Cl.
*G06K 9/62* (2006.01)
*A61B 6/00* (2006.01)
(Continued)

(52) U.S. Cl.
CPC ............ *A61B 6/5211* (2013.01); *A61B 6/504* (2013.01); *A61B 90/39* (2016.02); *G06K 9/342* (2013.01);
(Continued)

(58) Field of Classification Search
CPC .... A61B 6/504; A61B 5/02007–02021; A61B 2090/3735; A61B 3/102;
(Continued)

(56) References Cited

U.S. PATENT DOCUMENTS 5,357,550 A 10/1994 Asahina et al.
6,763,261 B2 7/2004 Casscells, III et al.
(Continued)

FOREIGN PATENT DOCUMENTS

JP 2010-526556 A 8/2010
JP 2013-000583 A 1/2013
(Continued)

OTHER PUBLICATIONS

Athanasiou, L.S., et al., "3D Reconstruction of Coronay Arteries using Frequency Domain Optical Coherence Tomography Images and Biplane Angiography", IEEE, Aug. 2012 (four pages).
(Continued)

*Primary Examiner* — Brian Werner
(74) *Attorney, Agent, or Firm* — Canon U.S.A., Inc. I.P. Division

(57) ABSTRACT

Detecting a vessel region in multiple angiographic image frames and defining a direction that perpendicularly intersects a longitudinal direction of the vessel region to improve co-registration between two imaging modalities. Motion of the vessel region is then detected based on the direction that intersects the longitudinal direction of the vessel region by evaluating positions of the vessel region in the multiple angiographic image frames. The method includes defining an area based on the detected motion and the detected vessel region, detecting a marker of an imaging catheter disposed in the vessel region within the area and performing co-registration based on the detected marker.

20 Claims, 30 Drawing Sheets

(51) Int. Cl.

| | |
|---|---|
| *G06T 7/30* | (2017.01) |
| *G06T 7/20* | (2017.01) |
| *A61B 90/00* | (2016.01) |
| *G06T 7/12* | (2017.01) |
| *G06K 9/34* | (2006.01) |
| *G06K 9/46* | (2006.01) |
| *G06T 7/00* | (2017.01) |
| *G06T 7/181* | (2017.01) |
| *G06T 7/11* | (2017.01) |
| *G06K 9/44* | (2006.01) |
| *G06K 9/00* | (2006.01) |

(52) U.S. Cl.
CPC .......... *G06K 9/4638* (2013.01); *G06T 7/0012* (2013.01); *G06T 7/12* (2017.01); *G06T 7/20* (2013.01); *G06T 7/30* (2017.01); *A61B 6/4441* (2013.01); *A61B 2090/363* (2016.02); *A61B 2090/3614* (2016.02); *A61B 2090/376* (2016.02); *A61B 2090/3735* (2016.02); *A61B 2090/3782* (2016.02); *A61B 2090/3966* (2016.02); *G06K 9/44* (2013.01); *G06K 2009/00932* (2013.01); *G06K 2209/05* (2013.01); *G06T 7/11* (2017.01); *G06T 7/181* (2017.01); *G06T 2207/10081* (2013.01); *G06T 2207/10116* (2013.01); *G06T 2207/20092* (2013.01); *G06T 2207/30101* (2013.01)

(58) Field of Classification Search
CPC ...... A61B 5/0066; A61B 6/5211–5252; A61B 2090/3966; G06T 2211/404; G06T 2207/30101–30104; G06T 7/0012–0016; G06T 2207/10101; G06T 7/30–38; G01R 33/5635

See application file for complete search history.

(56) References Cited

U.S. PATENT DOCUMENTS

| | | | |
|---|---|---|---|
| 7,978,916 | B2 | 7/2011 | Klingensmith et al. |
| 8,175,684 | B2 | 5/2012 | Vaillant et al. |
| 8,478,387 | B2 | 7/2013 | Xu |
| 8,565,859 | B2 * | 10/2013 | Wang ............... A61B 6/12 600/427 |
| 8,909,323 | B2 | 12/2014 | Baumgart |
| RE45,534 | E * | 6/2015 | Huennekens .......... A61B 8/543 |
| 9,121,926 | B2 | 9/2015 | Nair et al. |
| 9,138,147 | B2 | 9/2015 | Schmitt et al. |
| 9,286,673 | B2 | 3/2016 | Begin et al. |
| 9,292,918 | B2 | 3/2016 | Zagrodsky et al. |
| 9,295,450 | B2 | 3/2016 | Furuichi et al. |
| 9,301,687 | B2 | 4/2016 | Kemp |
| 9,307,926 | B2 | 4/2016 | Begin et al. |
| 9,351,698 | B2 * | 5/2016 | Dascal .................. G06T 7/11 |
| 9,462,950 | B2 | 10/2016 | Xu |
| 9,833,221 | B2 | 12/2017 | Hutchins et al. |
| 9,855,384 | B2 * | 1/2018 | Cohen ................. A61M 5/007 |
| 9,901,317 | B2 | 2/2018 | Shimamura et al. |
| 2008/0091171 | A1 | 4/2008 | Strommer et al. |
| 2010/0208957 | A1 | 8/2010 | Chen et al. |
| 2011/0230758 | A1 | 9/2011 | Eichler |
| 2014/0270436 | A1 | 9/2014 | Dascal et al. |
| 2014/0276011 | A1 | 9/2014 | Schmitt et al. |
| 2015/0131886 | A1 * | 5/2015 | Aben .................. A61B 8/5261 382/132 |
| 2015/0250438 | A1 | 9/2015 | Bozkaya et al. |
| 2015/0272442 | A1 | 10/2015 | Motafakker-Fard et al. |
| 2016/0099010 | A1 | 4/2016 | Sainath et al. |
| 2016/0171711 | A1 | 6/2016 | Gopinath et al. |
| 2016/0206267 | A1 * | 7/2016 | Shimizu ................. A61B 6/12 |
| 2016/0335766 | A1 | 11/2016 | Ambwani et al. |
| 2017/0020392 | A1 | 1/2017 | Xu |
| 2017/0024532 | A1 | 1/2017 | Gopinath et al. |

FOREIGN PATENT DOCUMENTS

| | | |
|---|---|---|
| JP | 2013-56113 A | 3/2013 |
| JP | 2015-093131 A | 5/2015 |
| JP | 2015-109968 A | 6/2015 |
| WO | 2008/013255 A1 | 1/2008 |
| WO | 2014175853 A1 | 10/2014 |
| WO | 2015/044979 A1 | 4/2015 |
| WO | 2015/045368 A1 | 4/2015 |

OTHER PUBLICATIONS

Blondel, C., et al., "Reconstruction of Coronary Arteries From a Single Rotational X-Ray Projection Sequence", IEEE Transactions on Medical Imaging, vol. 25, No. 5, May 2006, pp. 653-663.

Bourantas, C. V., et al., "A new methodology for accurate 3-dimensional coronary artery reconstruction using routine intravascular ultrasound and angiographic data: implications for widespread assessment of endothelial shear stress in humans", Euro Intervention, vol. 9, Apr. 2013, pp. 582-593.

Bourantas, C. V., et al., "Angiocare: An Automated System for Fast Three-Dimesional Coronary Reconstruction by Integrating Angiographic and Intracoronay Ultrasound Data", Catheterization and Cardiovascular Intervention, vol. 72, Apr. 2008, pp. 166-175.

Bourantas, C. V., et al., "Bioresorbable vascular scaffold treatment induces the formation of neointimal cap that seals the underlying plaque without compromising the luminal dimensions: a concept based on serial optical coherence tomography data", Euro Intervention, Oct. 2014, pp. 1-16.

Bourantas, C.V., et al., "A method for 3D reconstruction of coronary arteries using biplane angiography and intravascular ultrasound images", Computerized Medical Imaging and Graphics, vol. 29, Nov. 2005, pp. 597-606.

Cardenes, R., et al., "3D Reconstruction of Coronary Arteries From Rotational X-Ray Angiography", IEEE, May 2012, pp. 618-621.

Coskun, A. U., et al., "Reproducibility of Coronary Lumen, Plaque, and Vessel Wall Reconstruction and of Endothelial Shear Stress Measurements In Vivo in Humans", Catheterization and Cardiovascular Interventions, vol. 60, Sep. 2003, pp. 67-78.

Ellwein, L.M., et al., Optical Coherence Tomography for Patient-specific 3D Artery Reconstruction and Evaluation of Wall Shear Stress in a Left Circumflex Coronary Artery, Cardiovascular Engineering and Technology, vol. 2, No. 3, Sep. 2011, pp. 212-227.

Giannoglou, G. D., et al., "In-vivo validation of spatially correct three-dimensional reconstruction of human coronary arteries by integrating intravascular ultrasound and biplane angiography", Diagnostic methods, vol. 17, No. 6, Sep. 2006, pp. 533-543.

Hebsgaard, L., et al., "Co-registration of optical coherence tomography and X-ray angiography in percutaneous coronary intervention. The Does Optical Coherence Tomography Optimize Revascularization (DOCTOR) fusion study", International Journal of Cardiology, vol. 182, Mar. 2015, pp. 272-278.

Hoffmann, K. R., et al., "Biplane X-ray angiograms, intravascular ultrasound, and 3D visualization of coronary vessels", International Journal of Cardiac Imaging, vol. 15, Dec. 1999, pp. 495-512.

Horsley, E., "Imaging for the Future . . . Intravascular Optical Coherence Tomography", Sep. 10, 2016; from https://www.slideshare.net/ErnestHorsley/coronary-optical-coherence-tomography-oct-angio-coregistration-acr-and-metal-stent-optimisation-mso-softwarefrom.

Kang, D., et al., "Three-Dimensional Blood Vessel Quantification via Centerline Deformation", IEEE Transactions on Medical Imaging, vol. 28, No. 3, Mar. 2009, pp. 405-414.

Khaleel, H. H., et al., "A Review paper of 3D Surface Reconstruction of Coronary Arteries From Cardiovascular Angiography", 2012 International Conference on Advanced Computer Science Applications and Technologies (Acsat), pp. 419-435, Nov. 2012, DOI: Doi 10.1109/Acsat.2012.13.

Klein, H. M., et al., "3D-Surface Reconstruction of Intravascular Ultrasound Images Using Personal Computer Hardware and a Motorized Catheter Control", Cardiovascular Interventional Radiology, vol. 15, Mar.-Apr. 1992, pp. 97-101.

Kraus, M.F., et al., "Motion correction in optical coherence tomography volumes on a per A-scan basis using orthogonal scan pat-

(56) References Cited

OTHER PUBLICATIONS terns", Bio. Med. Express, vol. 3, No. 6, Jun. 1, 2012, pp. 1182-1199.
Kumar, R.P., et al., "3D multiscale vessel enhancement based centerline extraction of blood vessels", Medical Imaging 2013: Image Processing, Proc. SPIE vol. 8669, Mar. 2013 (ten pages).
Laban, M., et al., "ANGUS: A New Approach to Three-Dimensional Reconstruction of Coronary Vessels by Combined Use of Angiography and Intravascular Ultrasound", Computers in Cardiology, IEEE, Oct. 1995, pp. 325-238.
Li, Y., et al., "Impact of Side Branch Modeling on Computation of Endothelial Shear Stress in Coronary Artery Disease: Coronary Tree Reconstruction by Fusion of 3D Angiography and OCT", Journal of the American College of Cardiology, vol. 66, Issue No. 2, Jul. 2015, pp. 125-135.
Maehara, et al., "Assessment and Quantification of Stent Results by Intracoronary Optical Coherence Tomography", Intervent. Cardiol. Clin., vol. 4, Issue 3, Jul. 2015, pp. 285-294.
Prati, et al., "Clinical Impact of OCT Findings During PCI: The CLI-OPCI II Study", JACC: Cardiovascular Imaging, vol. 8, No. 11, Nov. 2015, pp. 1297-1305.
Reiber, J., et al., "QCA, IVUS and OCT in interventional cardiology in 2011", Cardiovascular Diagnosis and Therapy, vol. 1, No. 1, Dec. 2011, pp. 57-70.
Rivest-Hénault, D., et al., "Nonrigid 2D/3D Registration of Coronary Artery Models With Live Fluoroscopy for Guidance of Cardiac Interventions", IEEE Transations on Medical Imaging, vol. 31, No. 8, Aug. 2012, pp. 1557-1572.
Sarwal, A., et al., "Three dimensional reconstruction of coronary arteries from two views", Computer Methods and Programs in Biomedicine, vol. 65, Issue 1, Jan. 2001, pp. 25-43, ISSN: 0169-2607.
Shekhar, R., et al., "Fusion of Intravascular Ultrasound and Biplane Angiography for Three-Dimensional Reconstruction of Coronary Arteries", IEEE, Computers in Cardiology, Sep. 1996, pp. 5-8.
Slager, C. J., et al., "True 3-Dimensional Reconstruction of Coronary Arteries in Patients by Fusion of Angiography and IVUS (ANGUS) and Its Quantitative Validation", vol. 102, No. 5, Aug. 2000, pp. 511-516.
St Jude Web Page, "Optis Stent Optimization Software", Last updated Feb. 10, 2017: https://www.sjmglobal.com/professionals/resources-and-reimbursement/technical-resources/vascular/intravascular-diagnostics-and-imaging/intravascular-diagnostics-and-imaging-system-ffr-oct/optis-metallic-stent-optimization-software?halert=show&clset=92f57278-460e-4300-b7fe-89e52a04194f%3acadddb93-fcc4-47f2-8ceb-fd88f01ca17f (three pages included).
Subramanian, K. R., et al., "Accurate 3D reconstruction of complex blood vessel geometries from intravascular ultrasound images: in vitro study", Journal of Medical Engineering & Technology, vol. 24, No. 4, Jul./Aug. 2000, pp. 131-140.
Timmins, L. H., et al., "Framework to Co-register Longitudinal Virtual Histology—Intravascular Ultrasound Data in the Circumferential Direction", IEEE Transactions on Medical Imaging, vol. 32, No. 11, Nov. 2013, pp. 1989-1996.
Tu, S., et al., "Fusion of 3D QCA and IVUS/OCT", International Journal of Cardiovascular Imaging, vol. 27, Issue 2, Feb. 2011, pp. 197-207.
Tu, S., et al., "Assessment of obstruction length and optimal viewing angle from biplane X-ray angiograms", Int. J. Cardiovasc. Imaging, vol. 26, No. 1, Jan. 2010, pp. 5-17.
Tu, S., et al., "In vivo comparison of arterial lumen dimensions assessed by co-registered three-dimensional (3D) quantitative coronary angiography, intravascular ultrasound and optical coherence tomography", Int. J. Cardiovasc. Imaging, vol. 28, No. 6, Aug. 2012, pp. 1315-1327.
Tu, S., et al., "In Vivo Flow Simulation at Coronary Bifurcation Reconstructed by Fusion of 3-Dimensional X-ray Angiography and Optical Coherence Tomography", Circ. Cardiovasc. Interv., vol. 6, No. 2, Apr. 2013, pp. e15-e17 (5 pages included).
Van Der Giessen, A., et al., "3D fusion of intravascular ultrasound and coronary computed tomography for in-vivo wall shear stress analysis: a feasibility study", Int. J. Cardiovasc. Imaging, vol. 26, No. 7, Oct. 2010, pp. 781-796.
Wahle, A., et al., "Fusion of Angiography and Intravascular Ultrasound in vivo: Establishing the Absolute 3-D Frame Orientation", IEEE Transations on Biomedical Engineering, vol. 46, No. 10, Oct. 1999, pp. 1176-1180.
Wahle, A., et al., "Geometrically Correct 3-D Reconstruction of Intravascular Ultrasound Images by Fusion with Biplane Angiography—Methods and Validation", IEEE Transations on Medical Imaging, vol. 18, No. 8, Aug. 1999, pp. 686-699.
Yang, J., et al., "Novel Approach for 3-D Reconstruction of Coronary Arteries from Two Uncalibrated Angiographic Images", IEEE Transactions on Image Processing, vol. 18, No. 7, Jul. 2009, pp. 1563-1572.
Zhang, W., et al., "3D Vessel Tree Reconstruction from Rotational C-arm Projections by Multi-view Stereo Reconstruction", APCMBE 2008: 7th Asian-Pacific Conference on Medical and Biological Engineering, IFMBE Proceedings, vol. 19, Jan. 2008, pp. 434-441, ISBN: 1680-0737.
Giovanni Jacopo Ughi, et al., "Clinical Characterization of Coronary Atherosclerosis With Dual-Modality OCT and Near-Infrared Autofluorescence Imaging", JACC: Cardiovascular Imaging, Nov. 2016 (in press), pp. 1-11.
Oubel, et al., "Analysis of Intracranial Aneurysm Wall Motion and its Effects on Hemodynamic Patterns", Proc. SPIE, Medical Imaging, vol. 6511, Mar. 2007 (eight pages included).
Oubel, et al., "Analysis of Intracranial Aneurysm Wall Motion and its Effects on Hemodynamic Patterns", Proc. SPIE, vol. 6511, Medical Imaging 2007: Physiology, Function, and Structure from Medical Images, 65112A.
Dehkordi, et al., "Extraction of the Best Frames in Coronary Angiograms for Diagnosis and Analysis", J Med Signals Sens. Jul.-Sep. 2016; 6(3): 150-157.
Wang Peng, et al., "Image-based Co-Registration of Angiography and Intravascular Ultrasound Images", IEEE Transactions on Medical Imaging, vol. 32, No. 12, Dec. 2013, pp. 2238-2249.
Notification of Transmittal of ISR/WO, and International Search Report and Written Opinion, for PCT/US2018/043756 and notification of transmittal of the ISR/WO, dated Nov. 20, 2018.
Invitation to Pay Additional Fees for PCT/US2018/043743, dated Dec. 11, 2018.
Notification of Transmittal of ISR/WO, and International Search Report and Written Opinion, for PCT/US2018/043743 and notification of transmittal of the ISR/WO, dated Feb. 5, 2019.

* cited by examiner

METHOD FOR EVALUATING CARDIAC MOTION USING AN ANGIOGRAPHY IMAGE

CROSS-REFERENCE TO RELATED APPLICATIONS

This application relates, and claims priority, to U.S. Provisional Application Ser. No. 62/537,204, filed Jul. 26, 2017, and to U.S. Provisional Application Ser. No. 62/680,780, filed Jun. 5, 2018, which applications are hereby incorporated by reference herein in their entireties.

BACKGROUND

Field of the Disclosure

The present disclosure relates in general to processing angiography image data, and more particularly, to a method for evaluating cardiac motion using an angiography image.

Description of the Related Art

Percutaneous coronary intervention (PCI) has improved significantly by innovative imaging modalities such as coronary angiography and intravascular imaging. Coronary angiography provides longitudinal silhouettes of coronary arteries while intravascular imaging modalities provide cross-sectional information of coronary arteries. Intravascular imaging such as intravascular ultrasound (IVUS) and optical coherence tomography (OCT) provide more precise lesion information, e.g., lumen size, plaque morphology and implanted device, a system that enables physicians to connect between two different imaging modalities was developed. This connection process is called co-registration. Intravascular imaging such as OCT, is acquired during a cardiac cycle, the co-registration process may be influenced by cardiac motion.

Thus, there is a need in the art for improved co-registration between an angiography imaging modality and an intravascular imaging modality by evaluating cardiac motion using an angiography image to improve detection of a radiopaque marker in an angiography image.

SUMMARY

The present disclosure is directed to a method for evaluating cardiac motion and estimating cardiac cycle using angiography image data to improve detection of a radiopaque marker in an angiography image. Evaluating cardiac motion in an angiography image may improve co-registration between angiography imaging modality and intravascular imaging modality. The method for processing an angiographic image includes obtaining multiple angiographic image frames of a vessel region and multiple intravascular image frames acquired by an imaging catheter in the vessel region during pullback of the imaging catheter. Detecting a vessel region in each of multiple angiographic image frames, determining a longitudinal direction of the detected vessel region, defining a direction that intersects the longitudinal direction and detecting motion of the vessel region based on the direction by evaluating positions of the vessel region in the multiple angiographic image frames. The method also includes defining an area based on the detected motion and the detected vessel region in order to detect a marker of the imaging catheter in at least one of the multiple angiography image frames. The method may conclude by performing co-registration between the multiple angiographic image frames and the multiple intravascular image frames based on the detected marker.

Further features of the present disclosure will become apparent from the following description of exemplary embodiments with reference to the attached drawings.

DETAILED DESCRIPTION

The following description is of certain illustrative embodiments, although other embodiments may include alternatives, equivalents, and modifications. Additionally, the illustrative embodiments may include several novel features, and a particular feature may not be essential to practice the devices, systems, and methods described herein.

The present disclosure includes searching for one or multiple dark points also known as candidate points in each angiography frame and selecting a targeted marker from the candidate points. The candidate points may be found within an area where the coronary arteries move due to cardiac motion. Therefore, evaluating cardiac motion allows for more accurate selection of the targeted marker. A range of interest in which the candidate points may be searched is based on the cardiac motion. Then, selection of the targeted marker may result in improved co-registration between an angiography image and an intravascular image.

Figure 1:
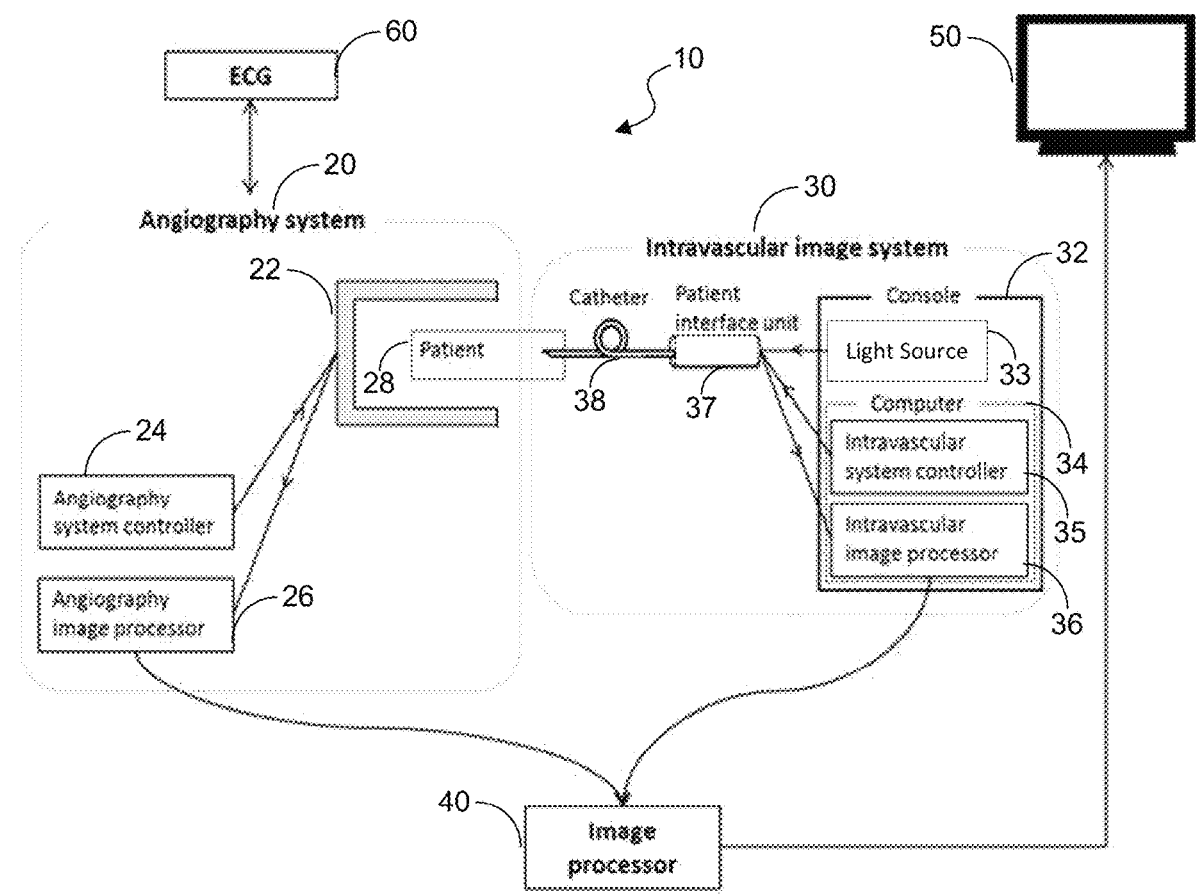
FIG. 1 is a schematic diagram illustrating an imaging system for executing various steps to process angiography image data in accordance with one or more aspects of the present disclosure.

Referring now to FIG. 1, shown is a schematic diagram of an exemplary imaging system 10. In the imaging system 10, an imaging catheter path may be generated based on either a directly detected location of a radiopaque marker on the imaging catheter or a regression line representing the imaging catheter path by using an angiography image frame that is simultaneously acquired during intravascular imaging pullback. The imaging system 10 includes an angiography system 20, an intravascular imaging system 30, an image processor 40, a display 50 and an electrocardiography (ECG) device 60. The angiography system 20 includes an X-ray imaging device such as a C-arm 22 that is connected to an angiography system controller 24 and an angiography image processor 26 for acquiring angiography image frames of a patient 28.

The intravascular imaging system 30 of the imaging system 10 includes a console 32, a catheter 38 and a patient interface unit 37 that connects between the catheter 38 and the console 32 for acquiring intravascular image frames. The catheter 38 is inserted into a blood vessel of the patient 28. The catheter 38 may function as a light irradiator and a data collection probe that is disposed in the lumen of a particular blood vessel, such as for example, a coronary artery. The catheter 38 typically includes a probe tip, one or more radiopaque markers, an optical fiber, and a torque wire. The probe tip may include one or more data collection systems. The catheter 38 is threaded in a patient's artery to obtain images of the coronary artery. The patient interface unit 37 has a motor inside to enable pullback of imaging optics during the acquisition of intravascular image frames. The imaging pullback procedure obtains images of the blood vessel. The imaging pullback path may represent the co-registration path which may be a region of interest or a targeted region of the vessel.

The console 32 includes a light source(s) 33 and a computer 34. The computer 34 includes an intravascular system controller 35 and an intravascular image processor 36. The intravascular image processor 35 controls the motor in the patient interface unit 37. The intravascular image processor 35 may also perform various steps for image processing and control the information to be displayed.

Various types of intravascular imaging systems may be used within the imaging system 10. The intravascular imaging system 30 is merely one example of an intravascular imaging system that may be used within the imaging system 10. Various types of intravascular imaging systems may be used including an OCT system, a multi-modality OCT system or an IVUS system by way of example.

The imaging system 10 may also include an electrocardiography (ECG) device 60 for recording the electrical activity of the heart over a period of time using electrodes placed on the skin of the patient 28. The imaging system 10 may also include an image processor 40 for receiving angiography data, intravascular imaging data and data from the ECG device 60 to execute various image processing steps to transmit to a display 50 for displaying an angiography image frame with a co-registration path. Although the image processor 40 associated with the imaging system 10 appears external to both the angiography system 20 and the intravascular imaging system 30, the image processor 40 may be included within the angiography system 20, the intravascular imaging system 30, the display 50 or a stand-alone device. Alternatively, the image processor 40 may not be required if the various image processing steps are executed using either the angiography image processor 26 or the intravascular image processor 36 of the imaging system 10.

Figure 2:
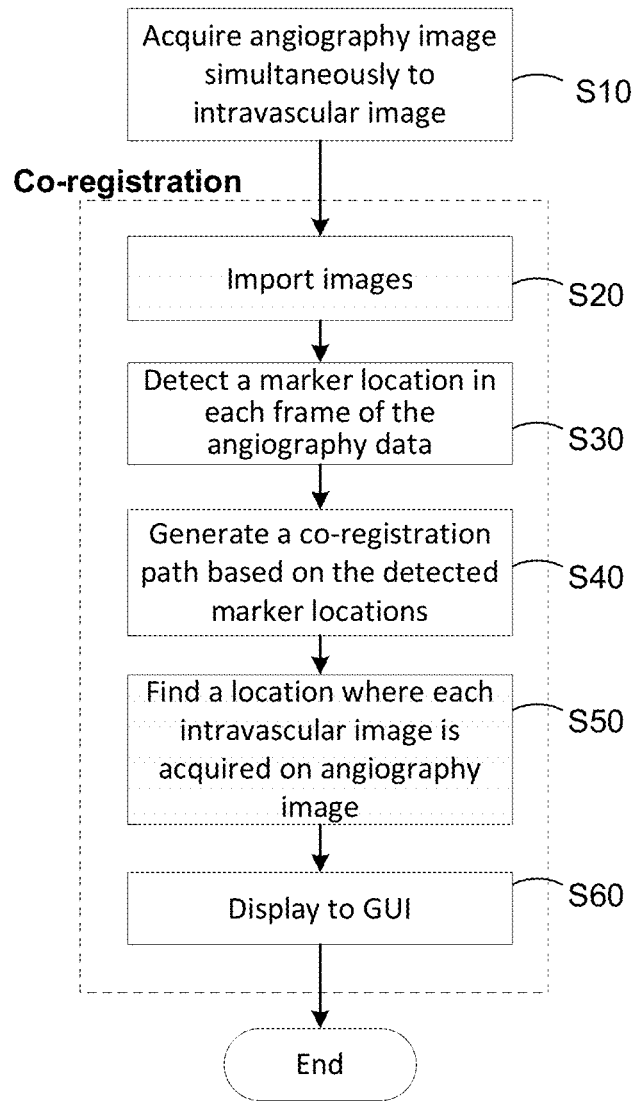
FIG. 2 is a flowchart illustrating various image processing steps in accordance with one or more aspects of the present disclosure.

Referring now to FIG. 2, a flowchart illustrating various steps for co-registering angiography data obtained from the angiography system 20 with intravascular imaging data obtained from the intravascular imaging system 30. The following steps for co-registration of angiography data with intravascular image data is applicable for a directly detected imaging catheter path as well as an imaging catheter path created as a regression line based on directly detected radiopaque marker locations based upon a regression line that is calculated. In the first step S10, angiography data such as angiography image frames are acquired simultaneously to the acquisition of intravascular image frames. Then, in step S20, the process for co-registration is initiated with importing both the angiography image frames and the intravascular image frames to an image processor. Subsequently, in step S30, a radiopaque marker location is detected for each angiography image frame from the angiography data. Each angiography image frame from the acquired angiography data may include a dark point that corresponds to the radiopaque marker of the catheter 38. The dark point that corresponds to the radiopaque marker of the catheter 38 is recognized by the image processor. The image processor stores the location of the radiopaque marker for each frame from a plurality of angiography image frames in a storage database.

In step S40, a co-registration path based on the detected radiopaque marker locations is generated. The co-registration path may represent the area where the image pullback is performed. The co-registration path may also represent a targeted region of a patient's coronary artery. The co-registration path may be generated for an entire angiography image frame or for selected one or multiple angiography image frames.

In step S50, a location where each intravascular image frame is acquired with respect to the angiography image frame is determined. In particular, a location is determined where each intravascular image is acquired in the global view of a coronary artery tree is searched using the information of the location of the detected radiopaque marker and the generated co-registration path. In step S60, the location where each intravascular image is acquired in the global view of the coronary artery tree is displayed on the angiography image frame within a GUI. The angiography image frame may also be displayed with an intravascular image frame. Each acquired intravascular image frame has an acquisition location, and it is visually represented on the displayed angiography image with the generated co-registration path. If a user prefers, the co-registration path can be selected not to overlay on the displayed angiography frame. After displaying within a GUI, the process for co-registering the angiography image frames and the intravascular image frames ends.

Figure 3:
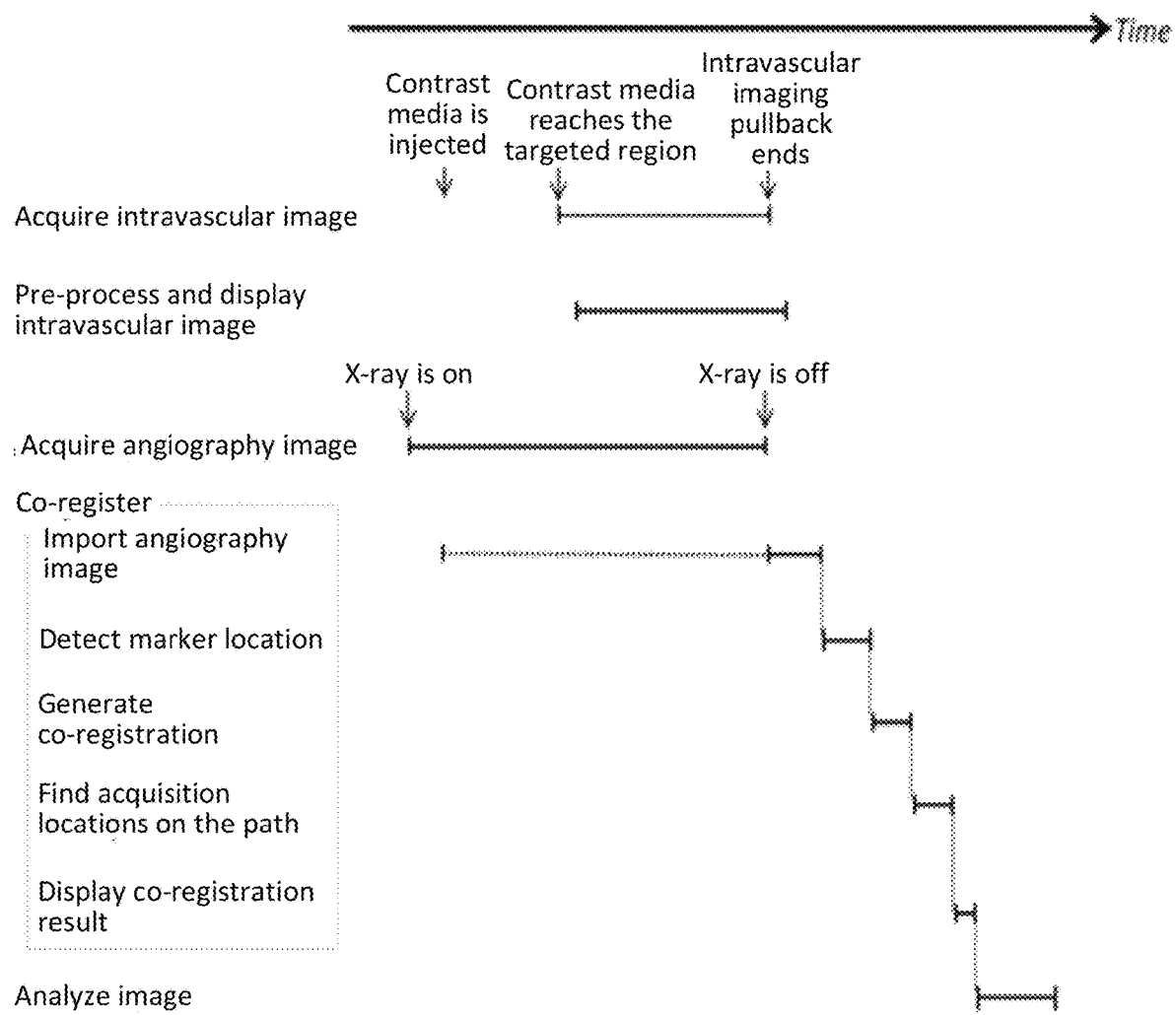
FIG. 3 is a time chart diagram illustrating a timing of a co-registration workflow in accordance with one or more aspects of the present disclosure.

Referring now to FIG. 3, a time chart illustrating at what point in time various steps associated with the co-registration process occur. Before referring to the various steps associated with the co-registration process, there are three events to note within the time chart. The first event corresponds to contrast media being injected into a patient's artery or blood vessel to clear the blood within the area where the intravascular image will be acquired. The contrast media may refer to a dye that is injected into the patient. Sometime after the contrast media is injected into the patient, the contrast media reaches the targeted region which corresponds to the second event along the time chart. A third event associated with the time chart includes the completion of an intravascular imaging pullback procedure which occurs after the contrast media reaches the targeted region of the patient.

The intravascular image frames are acquired when the contrast media reaches the targeted region of the patient and until the intravascular imaging pullback procedure is completed. Pre-processing and display of an intravascular image may occur in parallel to acquisition of the intravascular image frames with a certain time delay. The angiography data including angiography image frames are acquired when an X-ray is on until the X-ray is off. The acquisition of the angiography image frames may start before the contrast media reaches the targeted region of the patient. It is only necessary to acquire the angiography data until the third event where the intravascular imaging pullback procedure is completed. After the angiography data is acquired, the co-registration process may be initiated by importing the angiography data. The importing of the angiography data may occur after the intravascular imaging pullback procedure is completed.

The next step in the co-registration process includes detecting radiopaque marker locations for each angiography image frame. The detection of the radiopaque marker locations may occur after the angiography data is imported. Next, the co-registration path is generated after the radiopaque marker locations are detected for the angiography data. After generating the co-registration path the image processor may determine the acquisition locations of the intravascular image frames with respect to the co-registration path and the detected radiopaque marker location. Then, the angiography image frame and the intravascular image frame may be displayed on the monitor with overlaying the co-registration path and an artificial indicator representative of the acquisition locations of the intravascular image frames on the displayed angiography image frame. The displayed angiography image frame and intravascular image frame may be changed within the acquired angiography data and the intravascular data, along with the overlaying co-registration path and co-registration location. Both the angiography image frame and the intravascular image frame may appear as video that plays on the GUI. The displayed co-registration result is then analyzed by an interventional cardiologist by way of example.

Since the frame rate of intravascular image data is higher than that of the angiography image data, there are multiple intravascular frames of which acquisition location cannot be determined directly from the angiography image data by directly detecting radiopaque marker locations. Therefore, generation of a co-registration path is required to determine the acquisition locations for the intravascular image frames that do not have the corresponding angiography image frame.

Figure 4A:
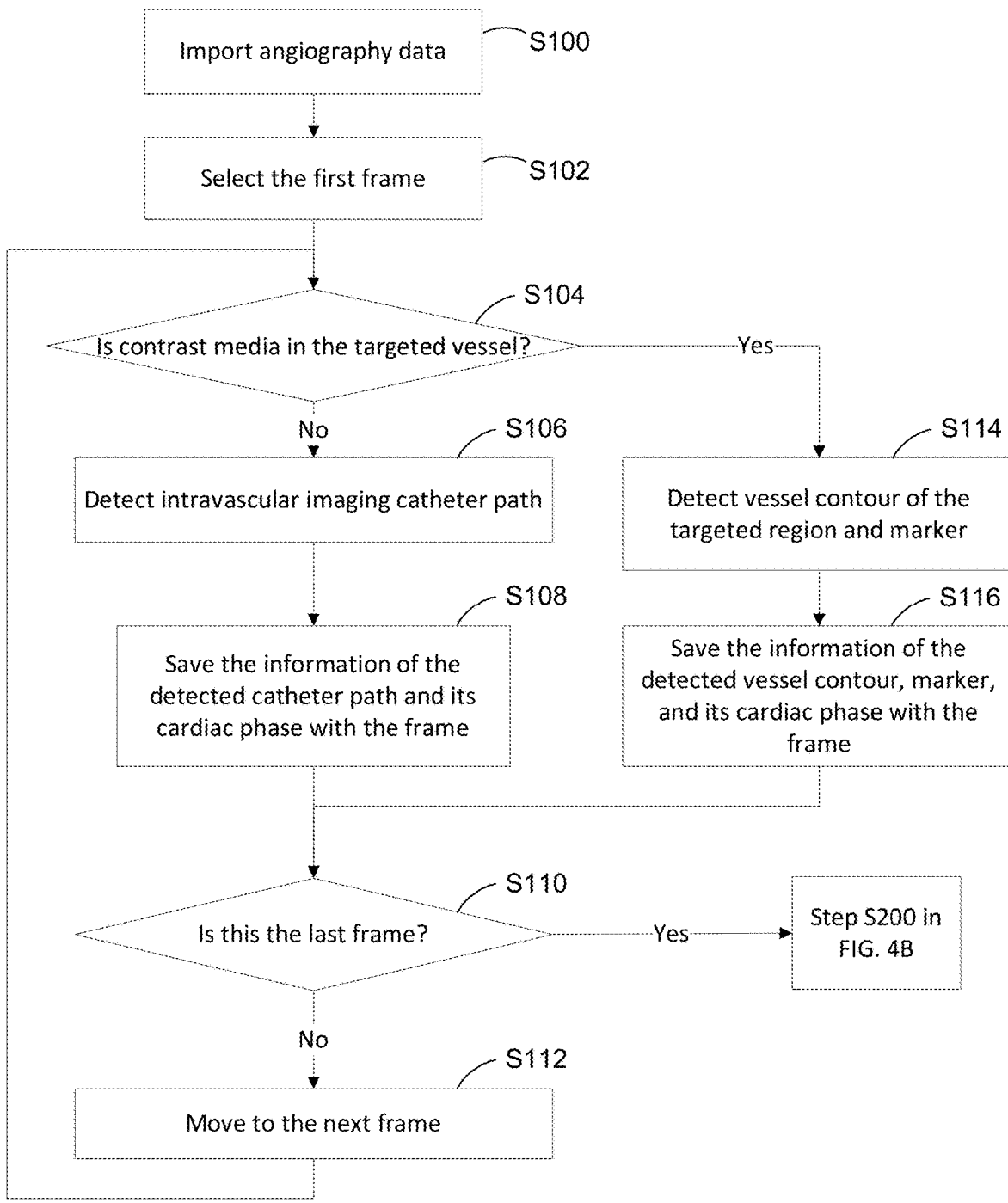
FIGS. 4A and 4B are flowcharts illustrating various steps for co-registration using a directly detected imaging catheter path in accordance with one or more aspects of the present disclosure.

Referring now to FIG. 4A, a flowchart illustrating various steps for generating a co-registration path based on an imaging catheter path that is directly detected. Since an imaging catheter path is used as the co-registration path, the accuracy of co-registration depends on the accuracy of the imaging catheter path generation. The advantage of using a directly detected imaging catheter path is that typically it is more accurate than other methods.

As an example, a guidewire over which the imaging catheter is delivered to the targeted vessel or a drive-cable of the imaging catheter can be used as the imaging catheter path. The imaging catheter path and the vessel contours can be detected by applying an edge detection filter, such as Sobel, Canny, Prewitt, Roberts, or others, and/or any combination from the edge detection filters. The radiopaque marker can be detected with, for example, Viterbi-based method or any edge detection method. The detected information is saved to each angiography image frame with the cardiac phase information. The cardiac phase information can be obtained by using estimated cardiac cycle information, of which estimation method is described below.

In step S100, the process is initiated with the importing of angiography data including angiography image frames.

Figure 4B:
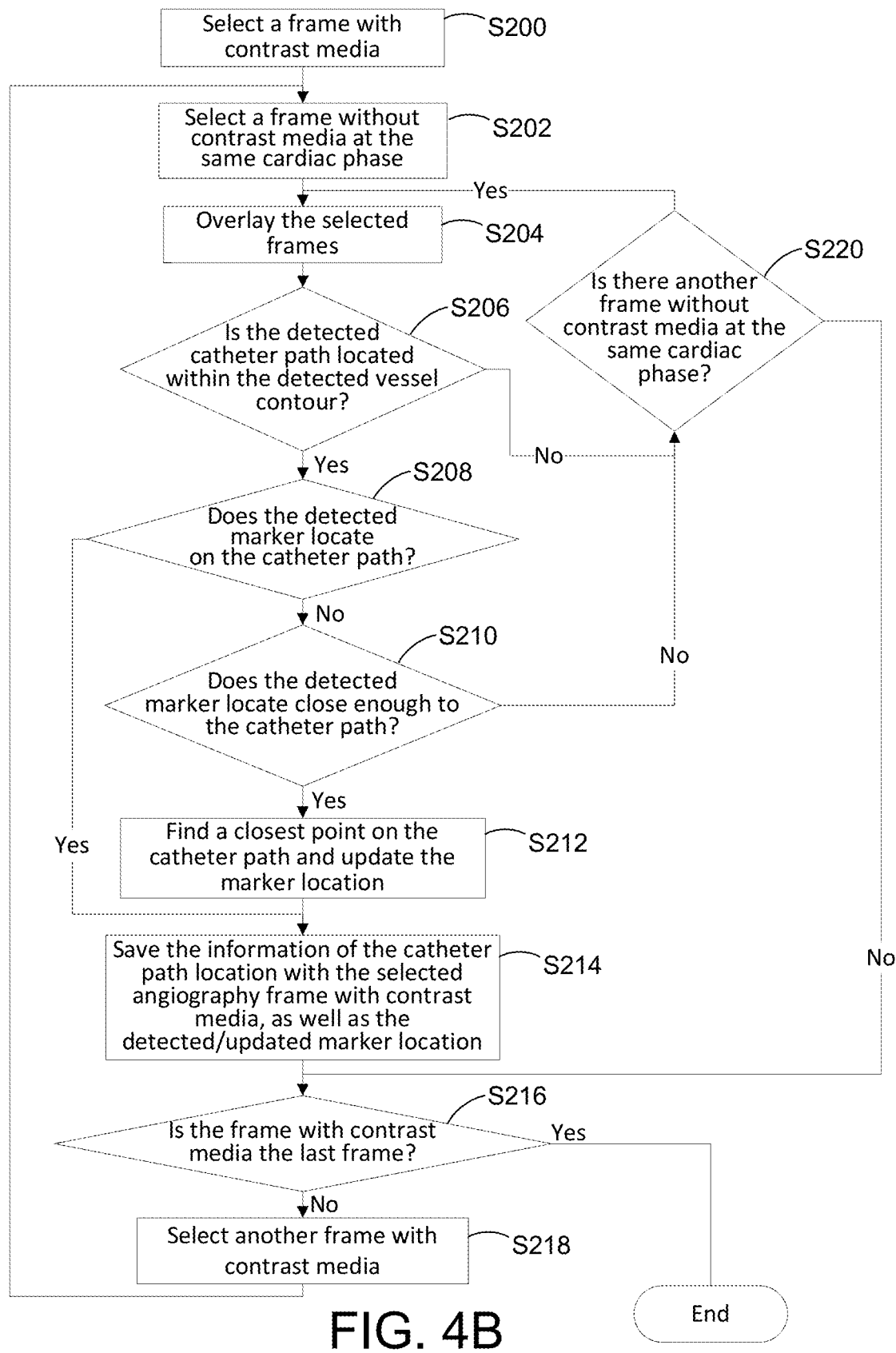

FIGS. 4A and 4B illustrate a case where the angiography image frames include the cardiac phase information (i.e., the angiography data are synchronized with the ECG signal) and there are enough angiography image frames without the contrast media in the targeted region of the blood vessel. In this case, the system can directly detect a co-registration path (i.e., an imaging catheter path). The accuracy of the imaging catheter path may be improved by the cardiac motion with the usage of the cardiac phase information and by checking the detected imaging catheter path location with detected radiopaque marker locations.

In step S102 a first angiography image frame is selected. In step S104, a determination is made with respect to whether there is contrast media in the targeted region of the blood vessel. To generate a directly detected imaging catheter path there are two requirements. The first requirement is including cardiac phase information associated with each angiography image frame. Cardiac phase information refers to an ECG signal synchronized with the angiography data. The second requirement includes a minimum quantity of angiography image frames that do not include contrast media in the targeted region of the blood vessel of a patient. Thus, in step S104 the determination of contrast media in the targeted region of the blood vessel divides the angiography image frames into two groups. One group of angiography image frames includes contrast media in the targeted region and another group of angiography image frames do not include contrast media in the targeted region. If there are not enough angiography image frames without the contrast media, then the imaging catheter path is determined using a regression line described below with respect to FIGS. 6A and 6B. The determination may be made based upon a predetermined threshold for angiography image frames without contrast media in the targeted region. The predetermined threshold may be automatically selected or inputted by a user of the imaging system 10 of FIG. 1.

The imaging system checks whether the imported angiography data has enough angiography image frames without the contrast media in the targeted blood vessel (i.e., the vessel region where the intravascular image is acquired). The imaging system may determine that the number of frames is sufficient if the angiography image frames without the contrast media are available for at least one cardiac cycle.

If it is determined in step S104 that the contrast media is not in the targeted region of the blood vessel, the first angiography image frame may be stored within the group of angiography image frames that do not include the contrast media in the targeted region and the process proceeds to step S106. In step S106, the imaging catheter path is detected for the first angiography image frame. In step S108, the information of the detected imaging catheter path and the cardiac phase associated with the first angiography image frame are saved with the first angiography image frame. After the detected imaging catheter path and the cardiac phase is saved with the first angiography image frame, it is determined whether the first angiography image frame is the last frame in step S110. In this example, the first angiography frame is not the last angiography image frame, the co-registration process proceeds to step S112 for selecting the next angiography image frame and the process returns to step S104. In this example, the next frame is the second angiography image frame and the steps are repeated until a last angiography image frame is selected.

Referring again to step S104 in FIG. 4A, if it is determined that there is contrast media in the targeted region of the blood vessel of the selected angiography image frame (Yes in step S104), the process proceeds to step S114. In step S114, the vessel contour of the targeted region and radiopaque marker are detected for the selected angiography image frame. Following step S114, the detected vessel contour, the detected radiopaque marker and the cardiac phase information associated with the selected angiography image frame are saved. Subsequently, it is determined in step S110 if the selected angiography image frame is the last frame. If it is determined that the selected angiography image frame is not the last frame (No in step S110), a next angiography image frame is selected in step S112 and the process returns to step S104.

In step S110, if it is determined that the selected angiography image frame is the last angiography image frame (Yes in step S110), the process proceeds to step S200 of FIG. 4B. Referring now to FIG. 4B, the flowchart illustrates various steps for determining whether the imaging catheter paths detected from one group of angiography image frames locate within the vessel contours detected from another group of angiography image frames in order to overlay the detected imaging catheter path onto the detected radiopaque marker.

In step S200, a first angiography image frame with contrast media is selected, and then in step S202 an angiography image frame without the contrast media that has the same cardiac phase as the first angiography image frame with contrast media is selected. In step S204, the two angiography images are overlaid. In step S206 it is determined whether the detected imaging catheter path is located within the detected vessel contour. If the detected imaging catheter path is located within the detected vessel contour (Yes in step S206), the process continues to step S208 to determine whether the detected radiopaque marker is located on the imaging catheter path. If it is determined in step S208 that the detected radiopaque marker is located on the imaging catheter path (Yes in step S208), the information of the imaging catheter path location is saved with the selected angiography image frame with the contrast media, as well as the detected radiopaque marker location in step S214. The process continues to step S216 where it is determined whether the selected first angiography image frame with the contrast media is the last angiography image frame with contrast media. If it is determined that the selected first angiography image frame with contrast media is not the last frame (No in step S216), then a next angiography image frame with contrast media is selected in step S218 and the process returns to step S202. Alternatively, if the selected angiography image frame with contrast media is the last frame (Yes in step S216), the process ends.

When it is determined in step S206 that the detected imaging catheter path is not located within the detected vessel contour (No in step S206), then it is determined whether there is another angiography image frame without contrast media at the same cardiac phase in step S220. If it is determined that there is another angiography image frame without contrast media at the same cardiac phase (Yes in step S220), then the process returns to step S204 and the new frame without contrast media at the same cardiac phase is overlaid with the selected angiography image frame with contrast media. Alternatively, if there is no angiography image frame without contrast media at the same cardiac phase (No in step S220), then the flowchart proceeds to step S216.

Returning to step S208, if it is determined that the detected radiopaque marker is not located on the imaging catheter path (No in step S208), it is then determined whether the detected radiopaque marker is located within a predetermined distance from the imaging catheter path in step S210. If the detected radiopaque marker is not within a predetermined distance of the imaging catheter path (No in step S210), the process returns to step S220. Alternatively, if the detected radiopaque marker is located within a predetermined distance from the imaging catheter path (Yes in step S210), then a closest point to the detected radiopaque marker on the imaging catheter path is updated as a marker location in step S212. Then in step S214, the updated marker location and the imaging catheter path location is saved with the selected angiography image frame with contrast media.

Figure 5:
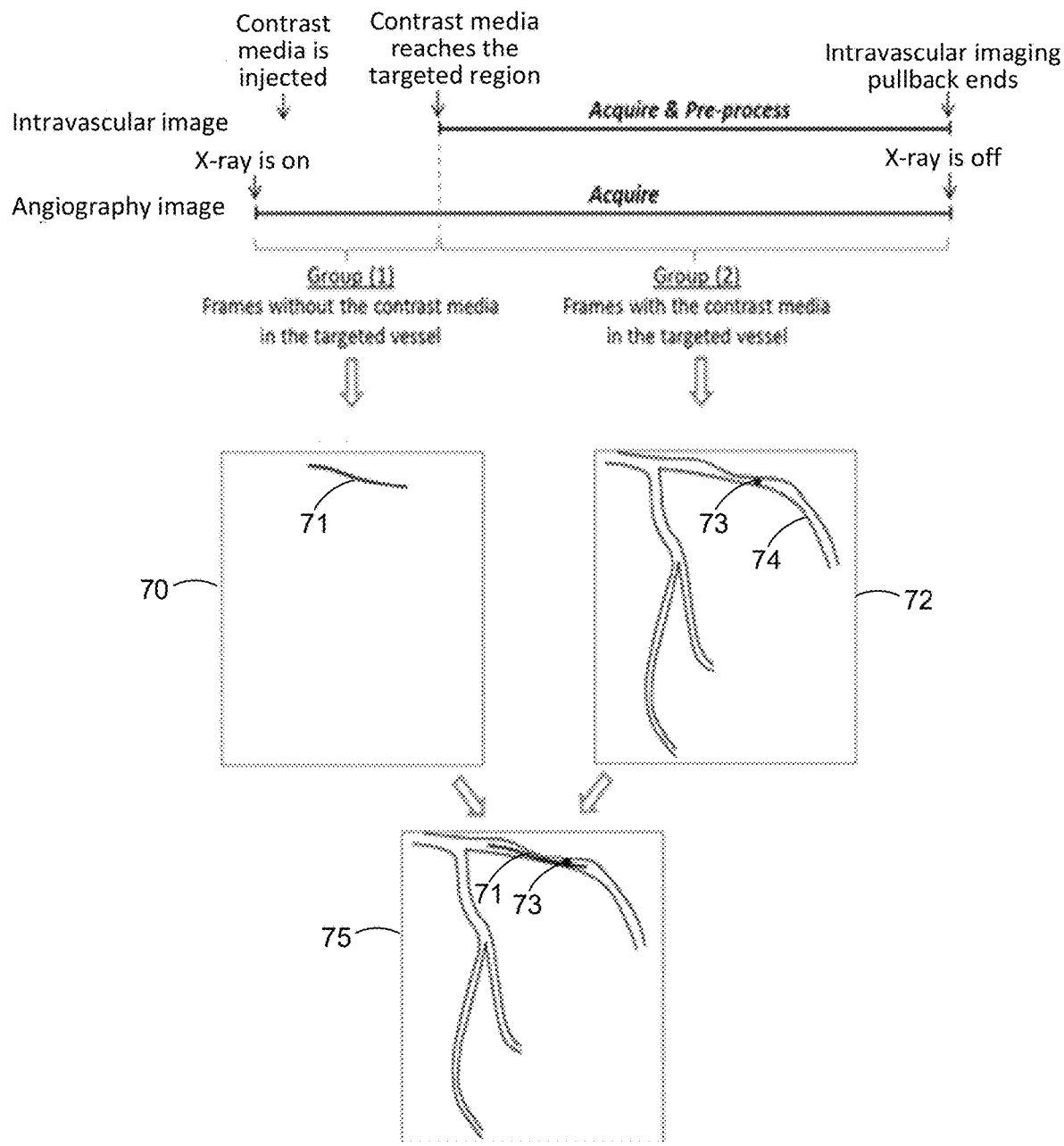
FIG. 5 is a visual representation of FIGS. 4A and 4B in accordance with one or more aspects of the present disclosure.

Referring now to FIG. 5 which illustrates the processes described in FIGS. 4A and 4B. The angiography data is acquired when an X-ray is on until the X-ray is off. The angiography data includes a plurality of angiography image frames which are divided into two different groups of angiography images frames. A first group of angiography image frames may include those angiography image frames without the contrast media in the targeted region of the targeted blood vessel. The first group of angiography image frames is acquired from the point where the X-ray is on until the contrast media reaches the targeted region. An image processor may be used to detect the imaging catheter path for the group of angiography image frames without the contrast media. The angiography image frame 70 includes an imaging catheter path 71 that is detected by the image processor.

The second group of angiography image frames may include angiography image frames with the contrast media in the targeted region of the targeted blood vessel. The angiography image frames with the contrast media are those angiography image frames that are acquired once the contrast media reaches the targeted region until the intravascular imaging pullback procedure is completed. The angiography image frame 72 includes the detected vessel contours 74 as well the detected radiopaque marker 73.

After the processes of detecting and saving for entire angiography image frames, the system chooses one angiography image frame from the group of angiography image frames with the contrast media and finds an angiography image frame with the same cardiac phase from the angiography image frames without the contrast media. Then, the imaging catheter path 71 detected from the selected angiography image frame 70 is overlaid on the selected angiography image frame 72 as shown in the angiography image frame 75 including the two overlaid angiography image frames (70, 72). The angiography image frame 75 is used to determine whether the detected imaging catheter path 71 is located within the detected vessel contours to make sure the detected imaging catheter path can be a representative line of the vessel's longitudinal direction. The angiography image frame 75 is also used to determine whether the detected radiopaque marker 73 is located on or within a certain distance from the detected imaging catheter path. Using the overlaid image 75, the system may determine whether the detected radiopaque marker is located on or within a certain distance from the detected imaging catheter path. The threshold of the distance can be predetermined by the system or determined by a user. If the overlaid image meets both criteria, the information of the detected imaging catheter path location is saved with the selected angiography frame with the contrast media. When the detected radiopaque marker is not located on the detected imaging catheter path but is located with a certain distance, the closest location to the detected radiopaque marker location on the imaging catheter path is searched, and its location is saved with the angiography frame with the contrast media by updating the detected marker location. If the overlaid image does not meet either one of the criteria, the system may search another angiography frame without the contrast media and follows the same process.

If there is no other angiography frame without the contrast media with the same cardiac phase, the system stops the process for the selected angiography frame with the contrast media. Then, the system selects another angiography image frame with the contrast media and repeats the entire process until the last frame with the contrast media is processed.

Figure 6A:
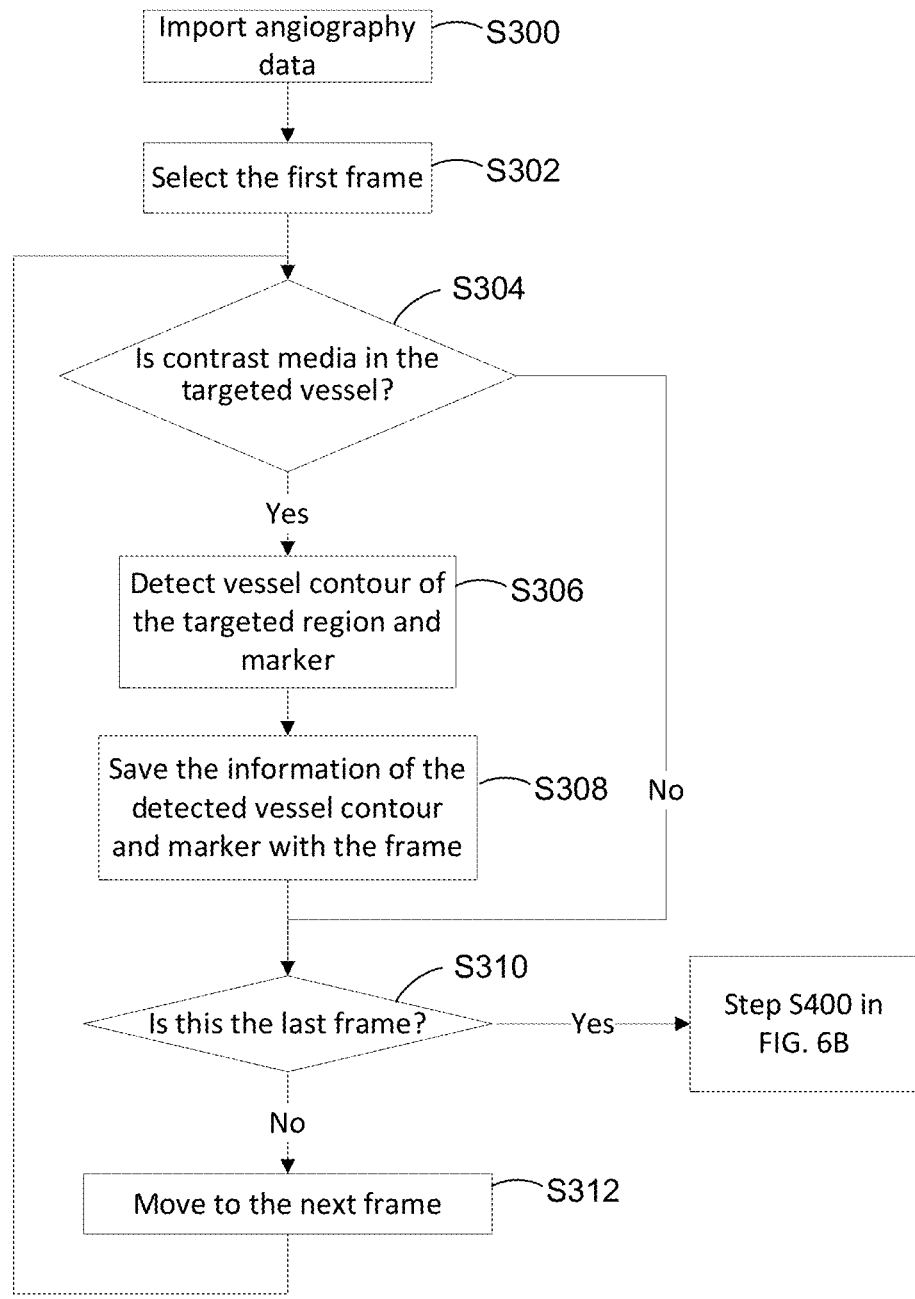
FIGS. 6A and 6B are flowcharts illustrating various steps for co-registration using an imaging catheter path based upon marker locations in accordance with one or more aspects of the present disclosure.
Figure 6B:
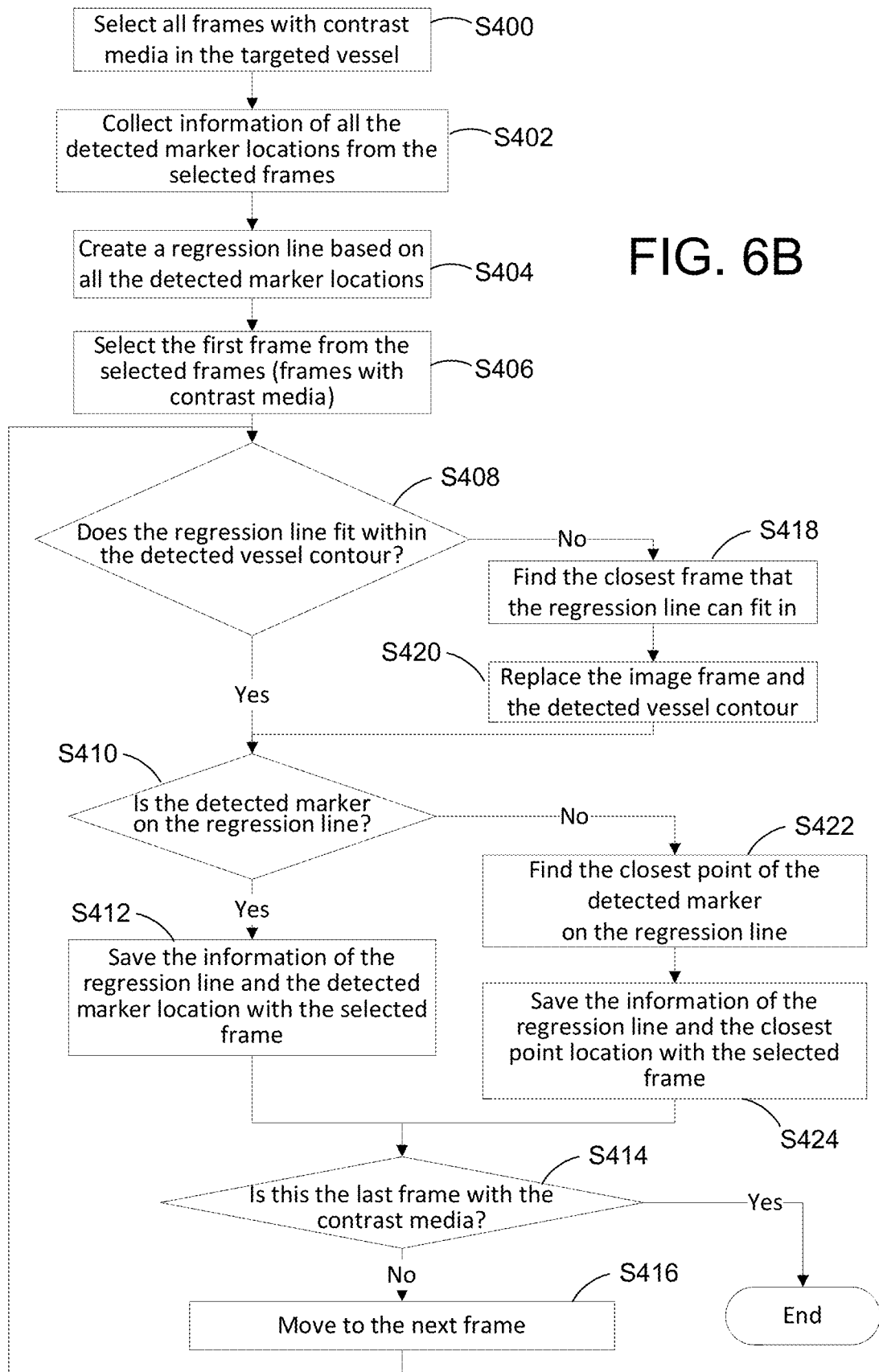

Referring now to FIGS. 6A and 6B, the flowcharts illustrate a case where the co-registration path is based on an imaging catheter path determined from a regression line that is based upon detected marker locations associated with the angiography data. The flowcharts of FIGS. 6A and 6B may be applied when the angiography data does include the cardiac phase information and/or when there are not enough angiography image frames without the contrast media in the targeted region of the blood vessel. In FIG. 6A, the process initiates with step S300 which includes importing angiography data that may include a plurality of angiography image frames. A first angiography image frame is selected in step S302. In step S304, it is determined whether contrast media is in the targeted region of the targeted blood vessel for the selected first angiography image frame. If it is determined that the contrast media is in the targeted vessel for the first angiography image frame (Yes in step S304), the vessel contour of the targeted region and the radiopaque marker are detected for the first angiography image frame selected in step S306. In step S308, the detected vessel contour and the radiopaque marker are saved with the first angiography image frame selected.

In step S310, it is determined whether the selected angiography image frame is the last angiography image frame. If the selected angiography frame is not the last frame (No in step S310), then in step S312, the next angiography frame is selected. In this example, the second angiography image frame is selected in step S312 and the process returns to step S304 until every angiography image frame has been selected. Alternatively, if in step S310 it is determined that the last frame is selected (Yes in step S310), the process proceeds to step S400 of FIG. 6B. Returning to step S304, if the angiography image frame that is selected does not include contrast media (No in step S304), then the process skips ahead to step S310.

In FIG. 6B, the process is initiated by selecting all angiography image frames with contrast media in the targeted vessel in step S400. Next in step S402, all the detected radiopaque marker locations from the selected angiography image frames are collected. In step S404, a regression line is generated based on all the detected radiopaque marker locations collected from the selected angiography image frames using, for example, least squares regression method. In step S406, a first angiography image frame is selected from the angiography image frames with contrast media. In step S408, a determination is made with respect to whether the regression line fits within the detected vessel contour of the selected angiography image frame with contrast media. In the case where the regression line fits within the detected vessel contour (Yes in step S408), it is then determined whether the detected radiopaque marker is located on the generated regression line in step S410.

If the detected radiopaque marker is on the regression line (Yes in step S410), the information associated with the regression line and the detected radiopaque marker location is saved with the selected angiography image frame in step S412. In step S414 it is determined whether the selected angiography image frame is the last frame with contrast media. If the selected angiography image frame is the last frame (Yes in step S414), then the process for generating a co-registration path is concluded. Alternatively, if it is determined that the selected angiography image frame is not the last angiography image frame with contrast media (No in step S414), a next frame is selected in step S416 and the process returns to step S408.

Returning now to step S408, if it is determined that the regression line does not fit within the detected vessel contour (No in step S408), the closest angiography image frame that the regression line can fit within the detected vessel contour associated with the closest frame is determined in step S418. Then in step S420, the closest angiography frame along with the detected vessel contour replaces the selected angiography image frame.

In step S410, if the detected radiopaque marker is not located on the regression line (No in step S410), then a point on the regression line closest to the detected radiopaque marker is determined in step S422. Then the location of the closest point on the regression line that is associated with the selected angiography frame is saved in step S424.

Figure 7:
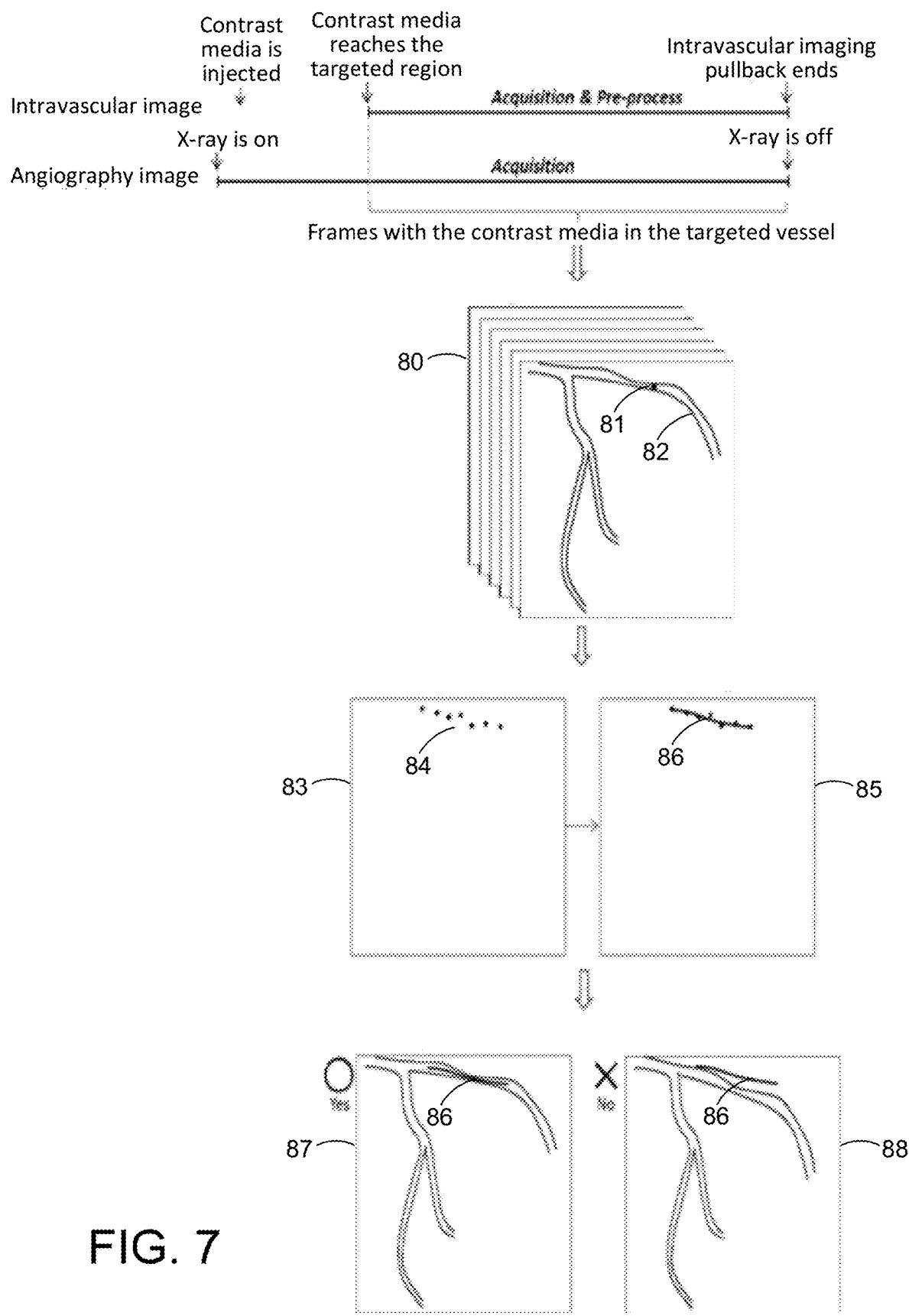
FIG. 7 is a visual representation of FIGS. 6A and 6B in accordance with one or more aspects of the present disclosure.

Referring now to FIG. 7, the angiography image frames 80 that include contrast media in the targeted region of a targeted blood vessel are grouped together. The angiography image frames 80 are the frames acquired once the contrast media reaches the targeted region until an intravascular imaging pullback procedure is completed. For each of the angiography image frames 80, an image processor may be used to detect the vessel contours 82 as well as the radiopaque marker 81. Then, all the information of the detected radiopaque marker locations 84 is collected and plotted in the same plane of the angiography image frame 83. Based on the detected radiopaque marker locations 84, a regression line 86 shown in the angiography image frame 85 is generated by using, for example, least squares regression method. After that, the system selects an angiography image frame from the previously selected angiography image frames and checks whether the regression line locates within the detected vessel contours. If the regression line 86 does not locate within the vessel contours as shown in the angiography image frame 88, the system searches another angiography image frame that the regression line 86 can locate within the vessel contours as shown in the angiography image frame 87 and that is acquired at the closest timing to the originally selected angiography image frame. The searched angiography image frame 87 with the closest timing replaces the originally selected angiography image frame. Upon replacement, the information of the detected vessel contours is also replaced, while the information of the detected radiopaque marker location is not replaced.

Then, the system checks whether the detected marker locates on the regression line. If the detected marker does not locate on the regression line, the system searches the closest location to the detected marker location on the regression line, and updates the information of the radiopaque marker location with the newly searched location. After that, the information of the detected or updated marker location and the regression line is saved with the selected angiography image frame. This process is repeated for each angiography image frame with the contrast media in the targeted region of the blood vessel. The process after generating a regression line can be performed in a different order. The system may first check whether the regression line locates within the detected vessel contours and update the angiography image frame if necessary for the group of angiography image frames with the contrast media. Then, the system can check whether the detected radiopaque marker locates on the regression line or not and updates its location if necessary.

Figure 8A:
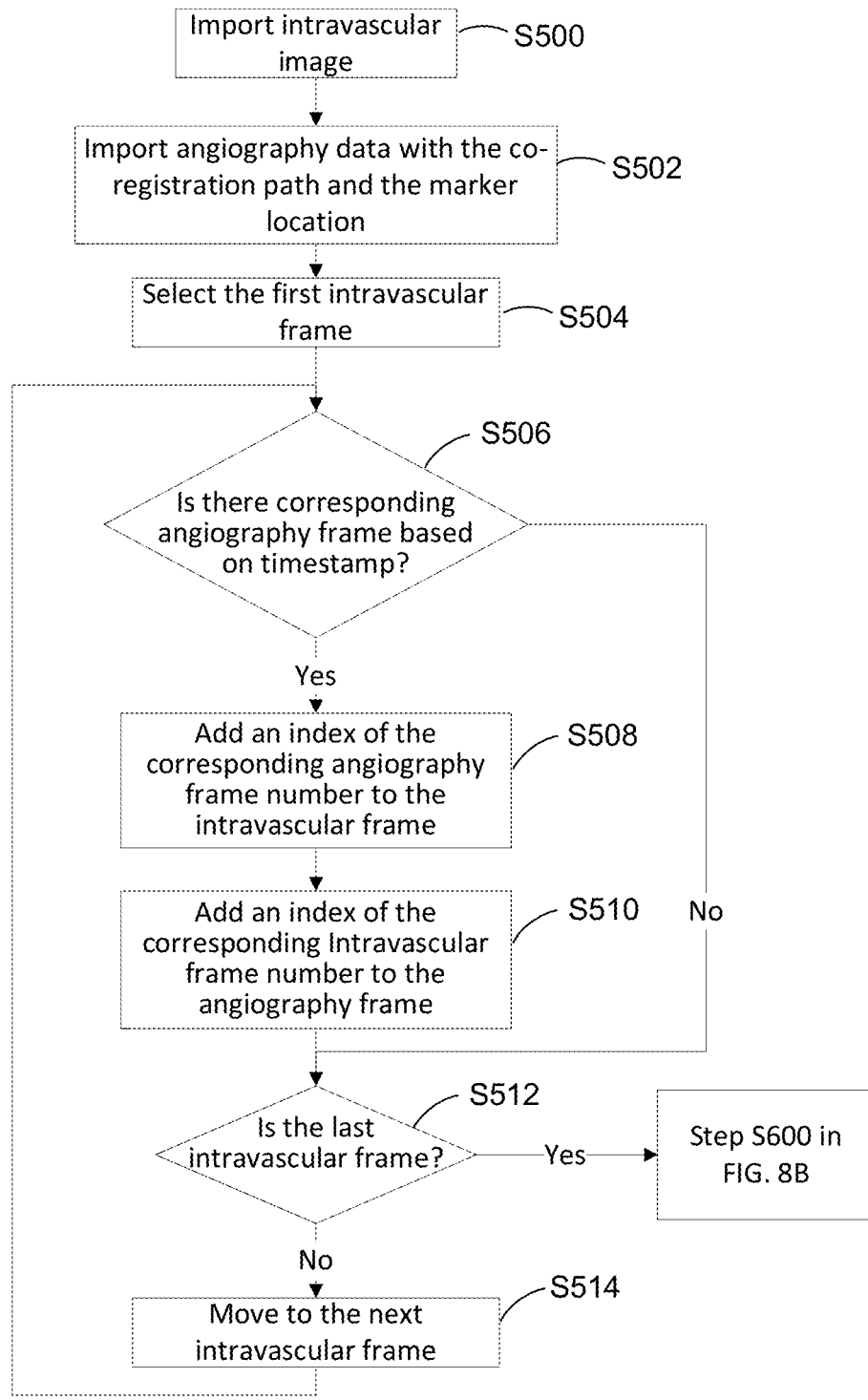
FIGS. 8A and 8B are flowcharts illustrating various steps for determining a location where acquired intravascular image frames are located on an angiography image frame in accordance with one or more aspects of the present disclosure.
Figure 8B:
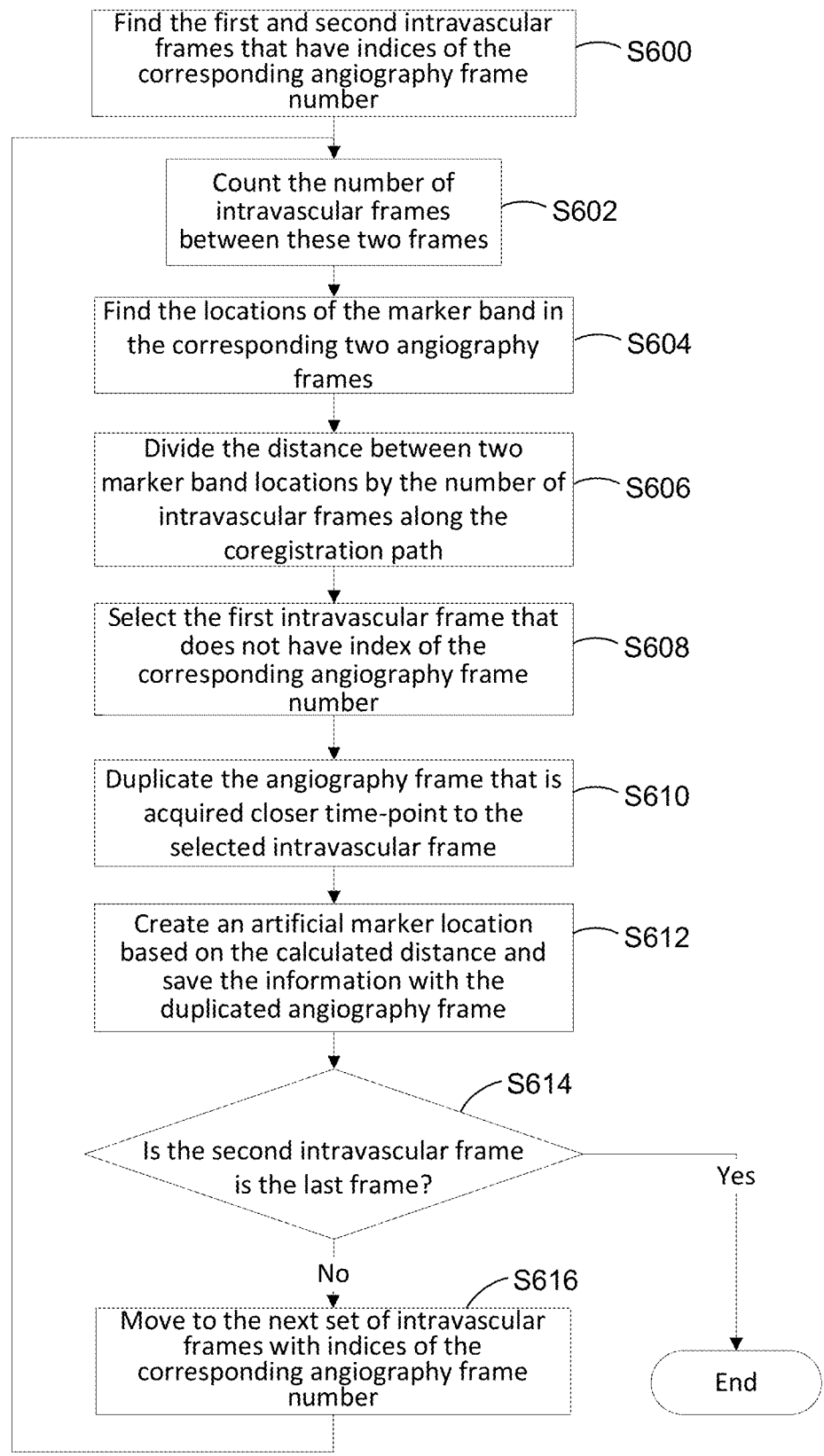

FIGS. 8A and 8B are flowcharts illustrating various steps to find an acquisition location of the intravascular image frame with respect to the angiography image frame. FIGS. 8A and 8B correspond to step S50 of FIG. 2. In step S500, the system imports intravascular image data including a plurality of intravascular image frames. In step S502, the angiography image frames with the co-registration paths and marker locations that were determined based on the co-registration steps outlined in FIGS. 4A & 4B or FIGS. 6A & 6B are imported. If the cardiac phase information was available as well as the requisite number of angiography image frames without contrast media, then the angiography image frames with the co-registration paths and marker locations that were determined based on the co-registration steps outlined in FIGS. 4A & 4B are imported. Alternatively, if the cardiac phase information was not available or there were not enough angiography image frames without the contrast media, then the angiography image frames with the co-registration paths and marker locations that were determined based on the co-registration steps outlined in FIGS. 6A & 6B are imported. In other words, the system includes the intravascular image frames and the angiography image frames with the co-registration path, either the directly detected imaging catheter path based on the steps outlined in the flowchart of FIGS. 4A & 4B or the newly generated imaging catheter path with the regression model, and the detected radiopaque marker locations based on the steps outlined in the flowchart of FIGS. 6A & 6B.

In step S504, a first intravascular image frame is selected. Next, in step S506 it is determined whether there is a corresponding angiography image frame based on the timestamp associated with the selected intravascular image frame. Initially the system may search the intravascular image frames that have the angiography image frames obtained at about the same time using the timestamps of both the intravascular image frame and the angiography image frame. If it is determined that there is a corresponding angiography image frame based on the timestamp (Yes in step S506), then, indices of the corresponding angiography frame number are added to the selected intravascular image frame in step S508, while the indices of the corresponding intravascular frame number are added to the angiography image frame in step S510. Alternatively, if it is determined that there is no corresponding angiography image frame based on the timestamp (No in step S506), then it is determined whether the selected intravascular image frame is the last intravascular image frame in step S512. If the selected intravascular image frame is not the last intravascular image frame (No in step S512), then a next intravascular image frame is selected in step S514 and returns to step S506. This process may be repeated until a last intravascular image frame is selected. If in step S512, it is determined that the selected intravascular image frame is the last intravascular image frame (Yes in step S512), then the flowchart continues to step S600 in FIG. 8B.

Referring now to FIG. 8B, a first and second intravascular image frames that have indices of the corresponding angiography image frame number are determined in step S600. In step S602, a number of intravascular image frames between the first and the second intravascular image frames are determined. Then, the locations of the radiopaque marker bands in the corresponding two angiography image frames are determined in step S604. In step S606, the distance between the two radiopaque marker band locations are determined and then divided by the number of intravascular image frames along the co-registration path that were determined in step S602. In step S608, a first intravascular image frame that does not have the index of the corresponding angiography frame number is selected. Then an angiography image frame that is acquired at a close time-point to the intravascular image frame selected in step S608 is duplicated in step S610. In step S612, an artificial marker location is generated based on the calculated distance and the information is saved with the duplicated angiography image frame. In step S614, it is determined whether the second intravascular image frame from step S600 is the last intravascular image frame. If the second intravascular image frame is not the last intravascular image frame (No in step S614), then a next set of intravascular image frames with indices of the corresponding angiography image frame number are selected in step S616, and the process returns to step S600. Alternatively, if the second intravascular image frame is the last intravascular image frame (Yes in step S614), then the process for finding an acquisition location of the intravascular image frame with respect to the angiography image frame is completed.

Figure 9:
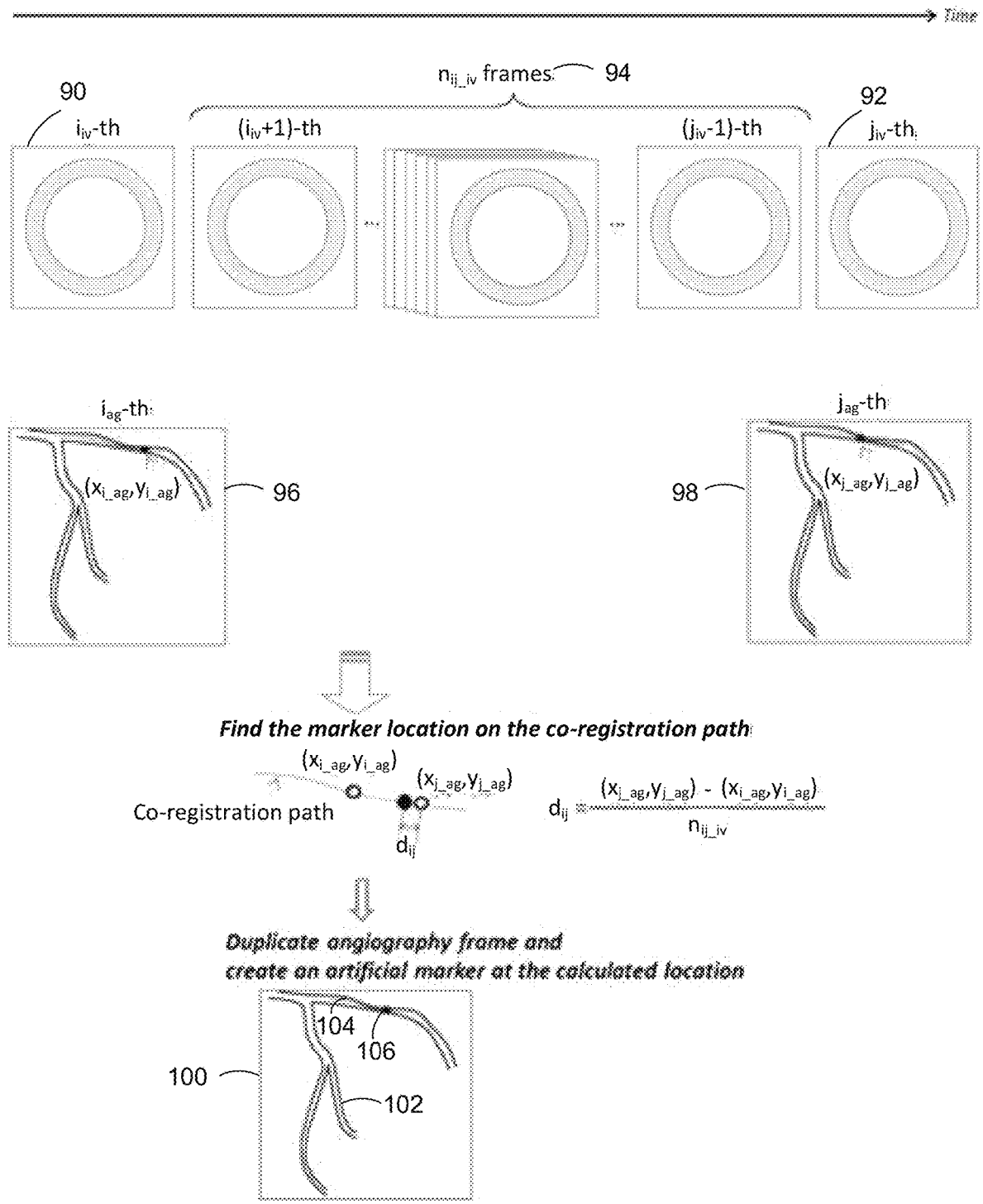
FIG. 9 is a diagram illustrating angiography image frames and intravascular image frames for determining a location of an acquired intravascular image frame on an angiography image frame in accordance with one or more aspects of the present disclosure.

Referring now to FIG. 9, the process outlined in the various steps of FIG. 8B are visually described. The system may find a first intravascular image frame 90 and a second intravascular image frame 92 [$i_{iv}$-th and $j_{iv}$-th frames] that have indices of the corresponding angiography image frame number, and counts the number of intravascular image frames between these two selected frames [$n_{ij\_iv}=j_{iv}-i_{iv}$] 94. The two corresponding angiography image frames are $i_{ag}$-th 96 and $j_{ag}$-th 98. Then, the system finds the corresponding radiopaque marker locations [($x_{i\_ag}$, $y_{i\_ag}$) and ($x_{j\_ag}$, $y_{j\_ag}$)] from the corresponding angiography image frames [$i_{ag}$-th and $j_{ag}$-th frame] (96, 98). Next, the system divides the distance between ($x_{i\_ag}$, $y_{i\_ag}$) and ($x_{j\_ag}$, $y_{j\_ag}$) by $n_{ij\_iv}$ along the co-registration path [$d_{ij}=\{(x_{j\_ag}, y_{j\_ag})-(x_{i\_ag}, y_{i\_ag})\}/n_{ij\_iv}$]. After that, the system selects the ($i_{iv}$+1)-th intravascular image frame and duplicates the angiography image frame 100 that is acquired at the closest timing on which the ($i_{iv}$+1)-th intravascular image frame is acquired.

When the angiography image frame 100 is duplicated, the imaging catheter path 104 is also duplicated. On the duplicated angiography image frame 100, the system generates a point 106 (i.e., an artificial marker) that locates at the calculated distance $d_{ij}$ from ($x_{i\_ag}$, $y_{i\_ag}$) along the co-registration path. The system then saves the artificial marker location on the duplicated angiography image frame 100 with the index of the corresponding intravascular image frame number. The system repeats these processes until it finishes them for ($j_{iv}$−1)-th intravascular image frame. Then, the system finds the second and the third intravascular image frames that have indices of the corresponding angiography image frame number, and repeats the above-described process. The process repeats until the system finishes with the second to last intravascular image frame and the last intravascular image frame that have the indices of the corresponding angiography frame number. The processes described above may be completed in a different order. The system can generate artificial markers every time it finds two intravascular image frames that have angiography image frames that are acquired at the same time.

In the method for generating a co-registration pair between the intravascular image frame and the angiography data, when ($i_{iv}$+1)-th intravascular image frame is selected, the angiography image frame is duplicated. However, in another method, the angiography image frame does not have to be duplicated. When ($i_{iv}$+1)-th intravascular image frame is selected, the angiography image frame that is acquired at the closest timing on which the ($i_{iv}$+1)-th intravascular image frame is acquired is searched, and its frame number is saved to the index of the ($i_{iv}$+1)-th intravascular image frame. Then, the acquisition location of the ($i_{iv}$+1)-th intravascular image frame is searched on the co-registration path using the same process described above. The searched location is saved to the ($i_{iv}$+1)-th intravascular image frame, along with the index of the angiography frame number.

Figure 10:
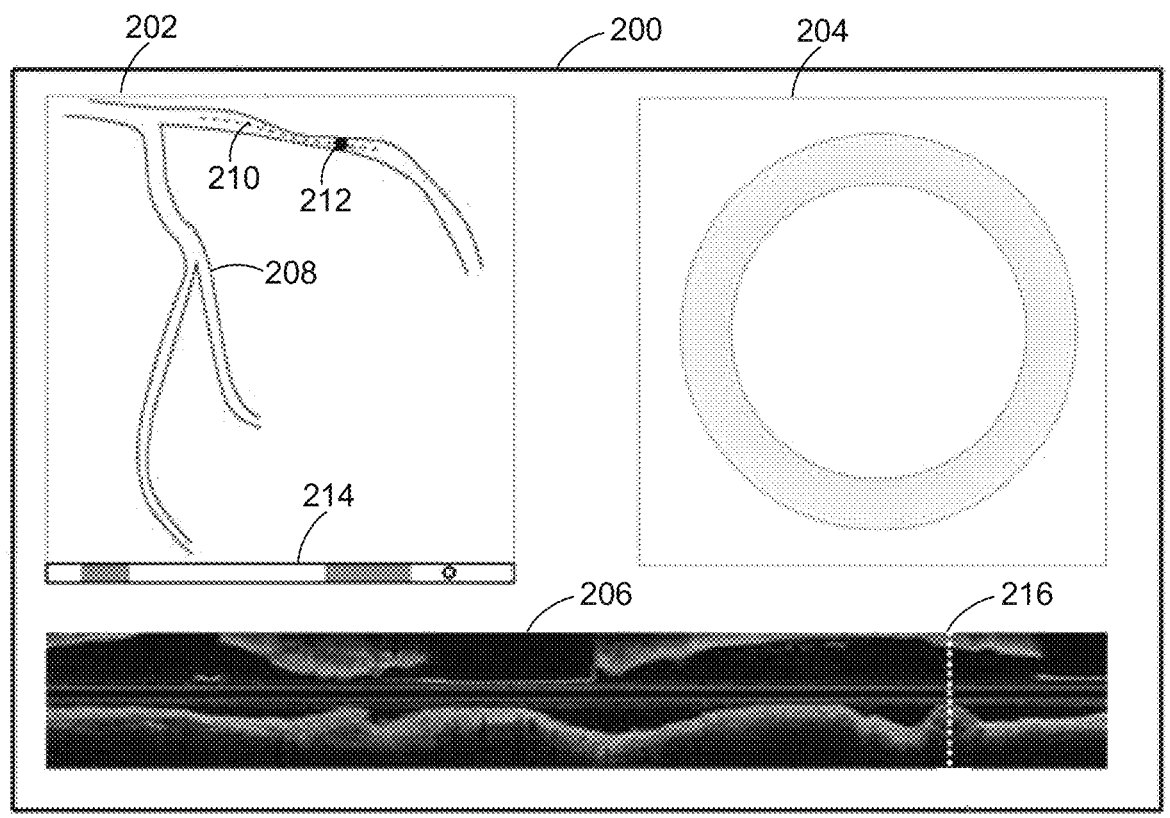
FIG. 10 is a diagram illustrating a graphical user interface for displaying a co-registration result in accordance with one or more aspects of the present disclosure.

Referring now to FIG. 10, the co-registration result may be displayed on a monitor or display using a graphical user interface (GUI) 200. The GUI may include the angiography image frame 202, the intravascular image frame 204 and a longitudinal view of a portion of the co-registration path 210. The co-registration path 210 is included in the angiography image frame 202 along with the vessel contours 208. The co-registration path 210 shows where the intravascular imaging pullback procedure was performed.

The system includes the intravascular image frame and the angiography image frame with the corresponding intravascular frame number. Once the intravascular image frame is selected by the system or by a user, the system searches the corresponding angiography frame using the indices of the angiography image frame and displays the angiography image frame on the monitor with an artificial indicator 212 overlaid on the angiography image frame. The artificial indicator 212 shows the position where the selected intravascular image frame 204 is acquired. The system also overlays the co-registration path 210 (i.e., the imaging catheter path that is directly detected or generated using a regression model) as its default setting, and a user can select not to display based on a user preference. In addition, the system displays the longitudinal view 206 of the targeted vessel. The longitudinal view is generated using the acquired intravascular image frame, and may have multiple patterns. In one example, the longitudinal view shows the location where the intravascular image frames was acquired using an artificial indicator 216.

The system also has an ability to check the reliability of co-registration. The intravascular image frames that have indices of the corresponding angiography image frame are numbered as $i_{iv}$-th, $j_{iv}$-th, $k_{iv}$-th, $l_{iv}$-th, . . . , and $z_{iv}$-th. The system chooses two intravascular image frames that have the indices of the corresponding angiography image frame number [for example, $i_{iv}$-th and $k_{iv}$-th frames]. These two frames should be apart at least one frame that has the index of the corresponding angiography frame number [in this example, $j_{iv}$-th frame is skipped]. Then, the system estimates the co-registration location for each of the intravascular image frames that are acquired between the two selected frames, $i_{iv}$-th and $k_{iv}$-th frames. After that, the estimated co-registration location(s) is compared to the actual co-registration location(s) that is directly detected (and updated) from the corresponding angiography image frame [in this example, the comparison is performed for the $j_{iv}$-th frame]. The difference between the actual and the estimated locations is considered as reliability value. If the reliability value exceeds a certain threshold, an alert may be shown on the monitor when the co-registration result is displayed. The threshold can be predetermined by the system, or can be determined by a user based on a user preference. An alert can be a text message on the display, and/or a graphical output, such as a color-coded indicator 214 and an indicator with different line style or different shape.

In another embodiment of the present disclosure, alternative methods are provided for imaging catheter path detection, step S106 in FIG. 4A, and for radiopaque marker detection, step S114 in FIG. 4A and step S306 in FIG. 6A.

First, a filter, e.g., homomorphic filter, is applied to reduce background noise that is created due to bone structure (e.g., ribs) and/or other organs (e.g., kidney). This process may be applied before step S104 in FIG. 4A or before step S304 in FIG. 6A.

Then, for step S106, i.e., the detection of imaging catheter path, an edge detection filter, such as Sobel, Canny, Prewitt, Roberts, or others, and/or any combination from the edge detection filters is applied, and the inner space of the dilated edges is filled. After that, a component(s) that contains the imaging catheter path is selected. The component selection can be done automatically by setting a pre-determined threshold or can be done semi-automatically by having one or multiple inputs from a user to specify the approximate location. Next, the selected component(s) is skeletonized. As a last step, the skeletonized result is smoothed by applying a smoothing function, for example, a cubic spline function or a polynomial fitting function.

For the detection of radiopaque marker, i.e., step S114 or step S306, after applying a filter to reduce the background noise, an edge detection filter, such as Sobel, Canny, Prewitt, Roberts, or others, and/or any combination from the edge detection filters is applied. Using the location information of the detected edge, the angiography image frame is masked to show only the area within the detected edges. Next, one or multiple dark points are searched in each masked angiography image frame. The number of points that are searched in each frame can be predetermined or can be set by a user, but it should be the same number throughout the angiography data.

After one or multiple dark points are searched in all the angiography image frames, the targeted radiopaque marker is determined for each frame. First, a user is asked to specify the approximate location of the radiopaque marker location in the first angiography image frame. Then, the targeted radiopaque marker is determined by searching the closest point from a point that a user inputs in the first angiography image frame. For the subsequent frames, the targeted radiopaque marker is determined by searching the closest point from the detected radiopaque marker location in the previous frame.

One or multiple dark points are searched and the determination of the targeted radiopaque marker can be done for each angiography image frame. In this case, the accuracy of radiopaque marker detection may be improved by narrowing down the searching area based on the targeted radiopaque marker location in the previous frame. Before searching one or multiple dark points, the angiography image frame is further masked to show only the area within the detected edges and proximal to the detected radiopaque marker location in the previous frame. A certain margin can be added to accommodate the movement of the targeted vessel due to cardiac motion. The margin can be predetermined by a system or can be set manually by a user.

A user input to specify the approximate location of the radiopaque marker location in the first angiography image frame can be obtained any time before the targeted radiopaque marker is determined in the first angiography image frame.

Then, for S106, i.e., the detection of imaging catheter path, an edge detection filter, such as Sobel, Canny, Prewitt, Roberts, or others, and/or any combination from the edge detection filters is applied, and the inner space of the dilated edges is filled. After that, a component(s) that contains the imaging catheter path is selected. The component selection can be done automatically by setting a pre-determined threshold or can be done semi-automatically by having one or multiple inputs from a user to specify the approximate location. Next, a curvature fitting function, such as a polynomial fitting function, is applied to either the selected component(s) or the detected edges within the selected component(s).

For the detection of the radiopaque marker, the determination of the targeted radiopaque marker can be achieved by tracking each searched point throughout the angiography data after one or multiple dark points are searched in all angiography image frames. Then, one or multiple dark points are searched in each angiography image frame. The number of points that are searched in each frame can be pre-determined or can be set by a user, but it should be the same number throughout the angiography data. Since the radiopaque marker moves in one particular direction during a pullback, i.e., from distal to proximal direction of the targeted vessel, the targeted radiopaque marker can be determined by finding one point that moves in the particular direction. For tracking, a Viterbi-based method or a Speeded Up Robust Features (SURF) method may be used by way of example.

Figure 11:
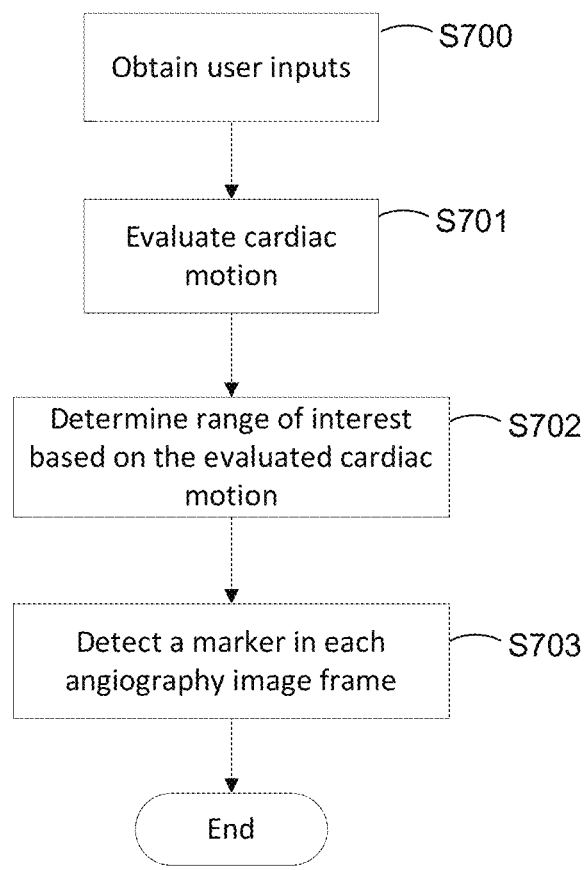
FIG. 11 is a flowchart illustrating various steps for detecting a marker in each angiography image frame while considering cardiac motion in accordance with one or more aspects of the present disclosure.

Intravascular imaging data and angiography data are acquired during multiple cardiac cycles. Since angiography data captures coronary artery tree in a global view and coronary arteries move within the cardiac cycle due to cardiac motion, co-registration may be affected by cardiac motion. Therefore, to improve co-registration results, especially detection of a marker in each frame of angiography data (step S30 in FIG. 2, S114 in FIG. 4A and S306 in FIG. 6A), the effects of cardiac motion need to be overcome. Estimation of the cardiac motion can be performed by selecting the angiography image frames that are captured within one or multiple cardiac cycle(s) that is specified based on the signals from the ECG device 60, or can be performed using entire angiography image frames. In the latter case, the ECG device 60 may not need to be included in the imaging system 10. At least for the purpose of improvement of co-registration results, the following processes can be used to estimate cardiac motion. FIG. 11 refers to a flowchart illustrating four different steps for overcoming the effects of cardiac motion on co-registration. The first step S700 involves obtaining user inputs to identify the location of the coronary artery in which intravascular imaging pullback is performed. Then, using the user inputs, the system evaluates cardiac motion in step S701 and defines a range of interest in step S702. Subsequently the system detects a marker within the range of interest in each angiography image frame in step S703.

There are a few different methods for the system to obtain user inputs in step S700. In a first method, the system shows one angiography image frame and asks a user to place inputs along the area within the vessel or close to the vessel where intravascular imaging pullback is performed from a distal to proximal end. The angiography image frame that is shown can be selected by the system such as the angiography image frame in which intravascular imaging pullback starts. Alternatively, a user may choose from the entire angiography data or adjust from the frame that is selected by the system.

In a second method for obtaining user inputs, the system shows multiple angiography image frames to a user. Multiple frames can be selected by the system based on a fixed number of frames to skip or based on cardiac cycle that is estimated with the angiography image or is determined via an ECG signal. The fixed number of frames to skip may be predetermined by the system or set by a user. A method to estimate the cardiac cycle with the angiography image is described in further detail below with reference to FIGS. 15-18. Once the cardiac cycle is estimated or determined, the system determines one or more cardiac phases, of which angiography image frames are shown to a user, within one or multiple cardiac cycles. A first angiography image frame that a user places one input or multiple inputs is shown automatically to the user, then a next angiography image frame is displayed once a user finishes placing user input(s) on the current frame. The number of user inputs to place per frame can be predetermined by the system or selected by the user. If only one user input per frame is allowed, the user preferably places an input on the marker that is shown as a darker point in the vessel. If multiple user inputs per frame are allowed, the user identifies the pullback region in the vessel from distal to proximal.

In this embodiment, user inputs are denoted as $ui_k$. $ui_1$ refers to the most distal user input, and as k increases, the user inputs moved towards the proximal direction. It is assumed that a user places m user inputs $ui_1$ to $ui_m$ on one frame for the method where only one angiography image frame is shown. For the method where multiple angiography image frames are shown, a user places total of m user inputs $ui_1$ to $ui_m$ on multiple frames when one user input per frame is allowed, and when multiple user inputs per frame are allowed, then m user inputs $ui_1$ to $ui_m$ on the first frame with total of m×n user inputs (where n is the number of multiple frames to be shown to the user) are placed. The system assumes that $ui_1$ is always located on or close to the location where the intravascular imaging pullback starts.

Figure 12:
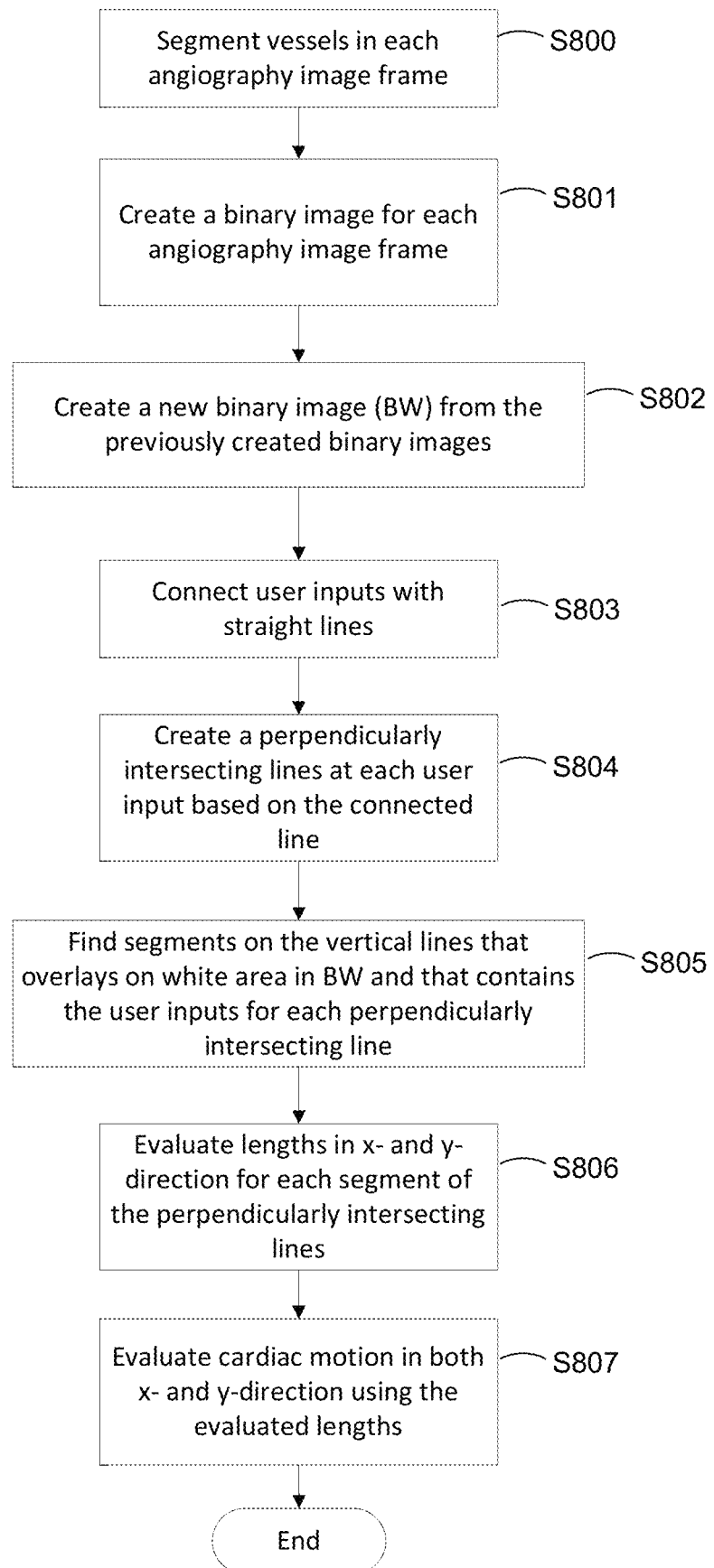
FIG. 12 is a flowchart illustrating various steps for evaluating cardiac motion in accordance with one or more aspects of the present disclosure.

FIG. 12 refers to a flowchart for evaluating cardiac motion as described in step S701 of FIG. 11. First, the system segments vessels in each angiography image frame in step S800. One method of segmenting the vessels is thresholding the angiography image frame. Since contrast media is injected in the vessels, the vessels look very dark in angiography data. The threshold value can be predetermined by the system or can be manually set or modified by a user. The threshold value can be the same for all the angiography image frames or can be different at each frame or at each group of frames. The area of the angiography image frame that is darker than a threshold value is assigned a binary value of 1 and the area of the angiography image frame that is not darker than a threshold value is assigned a binary value of 0. In this way, a binary image for each angiography image frame is generated according to step S801. Binary image data (bw data), of which frame correspond to each angiography image frame, is generated to show segmented vessel as white (value of 1) and other areas as black (value of 0). Based on bw data, a new binary image (BW) is generated in step S802. In the new binary image BW, white area represents the location of a segmented vessel in at least one of the angiography image frames.

To generate BW, in one example, the system can add all the frames of bw data. Then, the system connects between consecutive user inputs with straight lines in step S803. The straight lines that connected the consecutive user inputs may define the longitudinal direction of the vessel in which intravascular imaging pullback is performed. Based on the connected line, a direction that perpendicularly intersects the pullback direction is generated at each user input location in step S804. Those directions are defined by lines, each of which crosses each user input ($vl_1$ to $vl_m$). At the first and last user inputs ($ui_1$ and $ui_m$), line at $ui_1$ (i.e., $vl_1$) or $ui_m$ (i.e., $vl_m$) intersects perpendicularly to the connected line between $ui_1$ and $ui_2$ or between $ui_{m-1}$ and $ui_m$, respectively. At the other user inputs ($ui_k$, 1<k<m), line (i.e., $vl_k$) intersects perpendicularly to a straight line that directly connects $ui_{k-1}$ and $ui_{k+1}$. After defining the lines that intersect perpendicularly, the segment on the lines that intersect perpendicularly that overlays on white area in BW and that contains the user inputs is searched for each line in step S805. Then, since the lines that intersect perpendicularly are not parallel to the x-axis or y-axis, lengths that are projected to the x-axis and y-axis are evaluated for each segment of the intersecting lines ($CMx_1$, $CMy_1$ to $CMx_m$, $CMy_m$) in step S806. In step S807, the cardiac motion in both the x and y directions (CMx, CMy) is evaluated using the evaluated lengths $CMx_1$, $CMy_1$ to $CMx_m$, $CMy_m$. CMx, CMy can be the average of $CMx_1$ to $CMx_m$ and $CMy_1$ to $CMy_m$, or maximum value of $CMx_1$ to $CMx_m$ and $CMy_1$ to $CMy_m$. Although steps S803 and S804 are shown to occur after steps S800-S802 in FIG. 12, steps S803 and S804 may be performed prior to steps S800-S802. Additionally, step S800 may be performed before obtaining user inputs in step S701 of FIG. 11.

Figure 13:
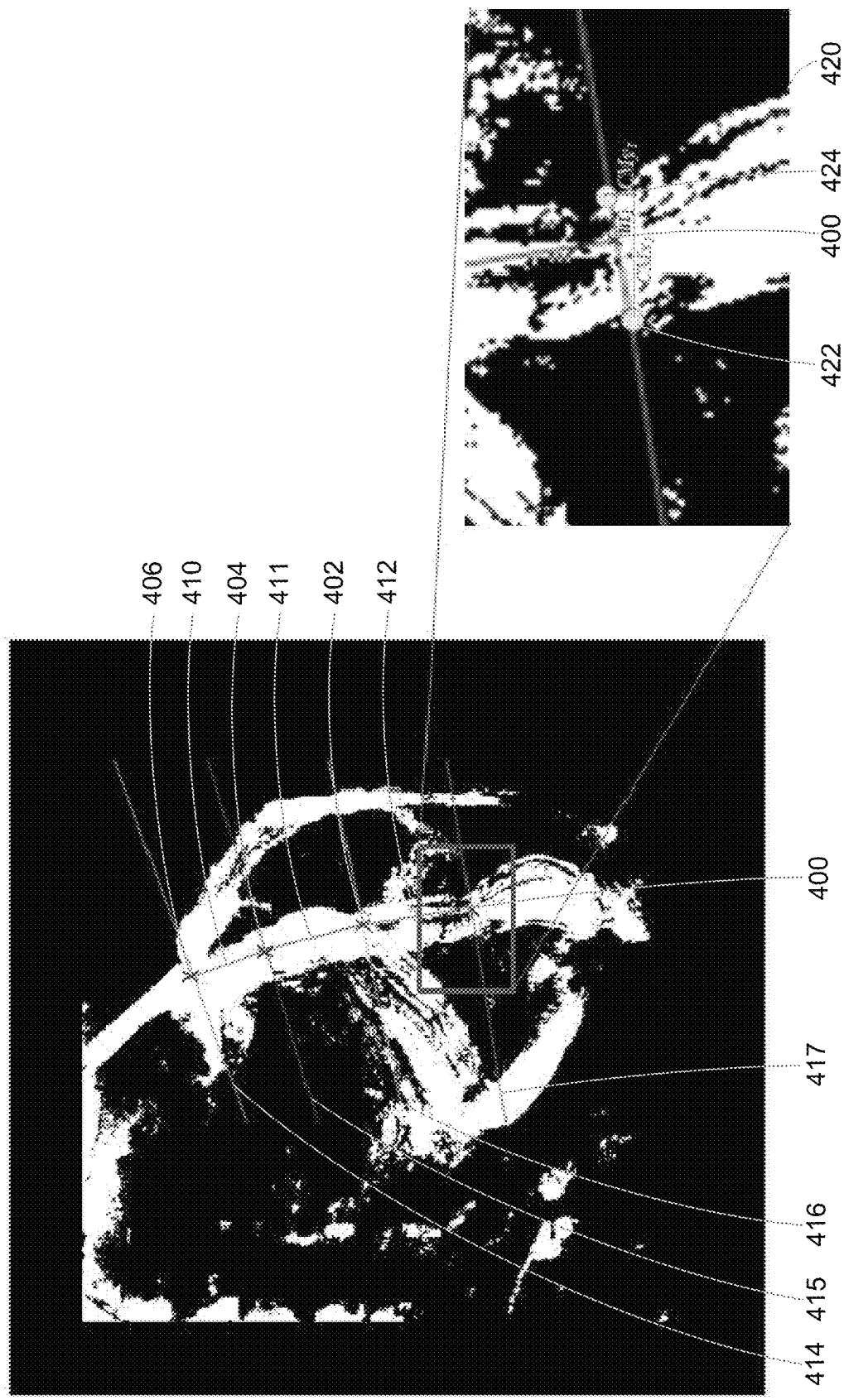
FIG. 13 illustrates a schematic diagram of a binary image in accordance with one or more aspects of the present disclosure.

FIG. 13 is an example of a binary image BW as described above with reference to FIG. 12. In the binary image, four different user inputs are shown starting from a distal end $ui_1$ 400 to a proximal end $ui_4$ 406 with $ui_2$ 402 and $ui_3$ 404 in between. The lines 410-412 that connect the consecutive user inputs define the longitudinal direction of the vessel where intravascular image pullback has occurred. The lines 414-417 that intersect each user input perpendicularly are then evaluated to determine the cardiac motion. For example, FIG. 13 provides a zoomed in view 420 of $ui_1$ 400 to show cardiac motion in the x-direction 422 and cardiac motion in the y-direction 424 for the first user input ($CMx_1$, $CMy_1$).

Figure 14:
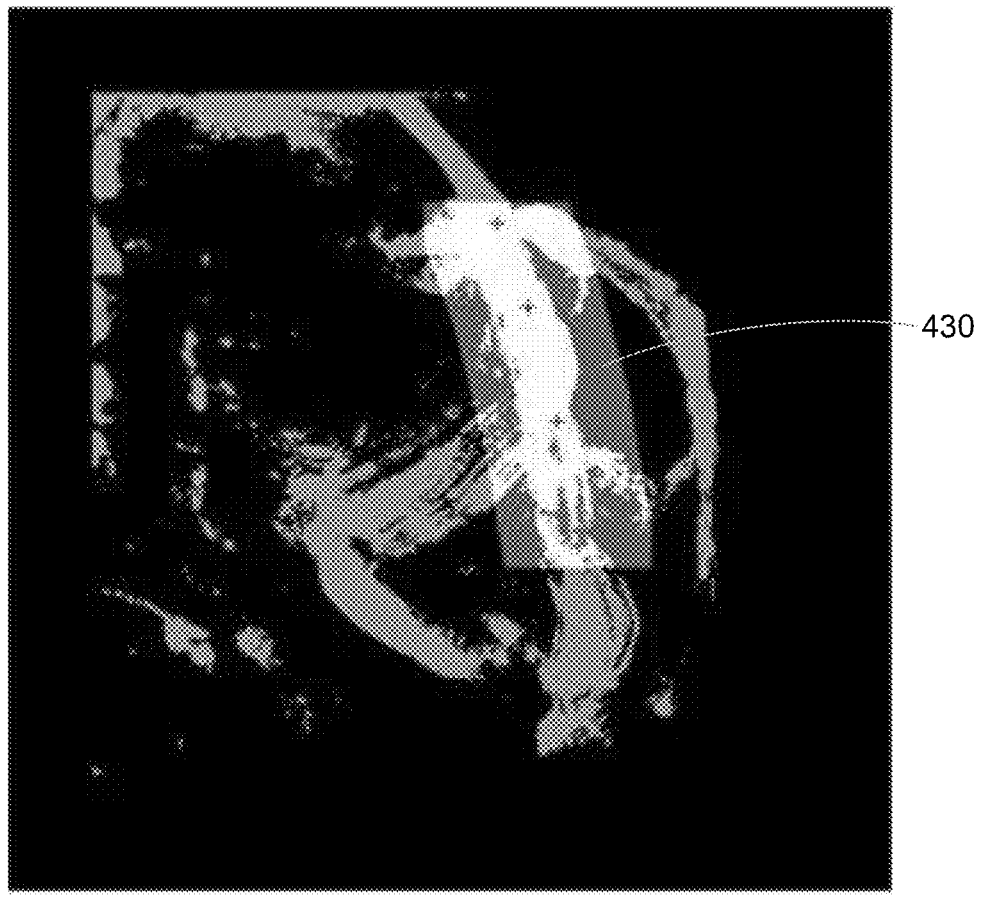
FIG. 14 illustrates a region of interest within the binary image of FIG. 13 in accordance with one or more aspects of the present disclosure.

After step S701, the range of interest is defined using the connected line and the evaluated cardiac motion CMx 422, CMy 424. First, a binary image that shows the connected line as white area is generated as shown in FIG. 13. Then, the connected line is dilated with CMx in the x-direction and with CMy in the y-direction. The white area after the dilation is defined as the range of interest in further processing and as shown in FIG. 14 within the shaded region 430.

In step S703 of FIG. 11 to detect a marker, first, candidate points, i.e., dark points, within the segmented vessel within the defined range of interest are searched for each angiography frame. The number of candidate points may be predetermined by the system or set by the user. Then, a targeted marker is selected from the candidate points. The selection of the targeted marker includes choosing the closest point from the targeted marker in the previous frame, by finding one point that moves in the particular direction (i.e., proximal to distal direction), or by finding the closest point from the estimated targeted marker location. The estimation of the targeted marker may be performed using the user input locations, the pullback speed and the evaluated cardiac motion. Based on the user inputs, the region of intravascular pullback in the vessel is defined. Since $ui_1$ is located near the beginning of the intravascular pullback, the movement of the marker from the first frame to the next frame until the end of pullback can be estimated along the connected line or the segmented vessel from the $ui_1$ location. Then, the movement due to cardiac motion is considered by adding the evaluated cardiac motion information and potentially adding an evaluation of cardiac phase with the estimated cardiac cycle.

Figure 15:
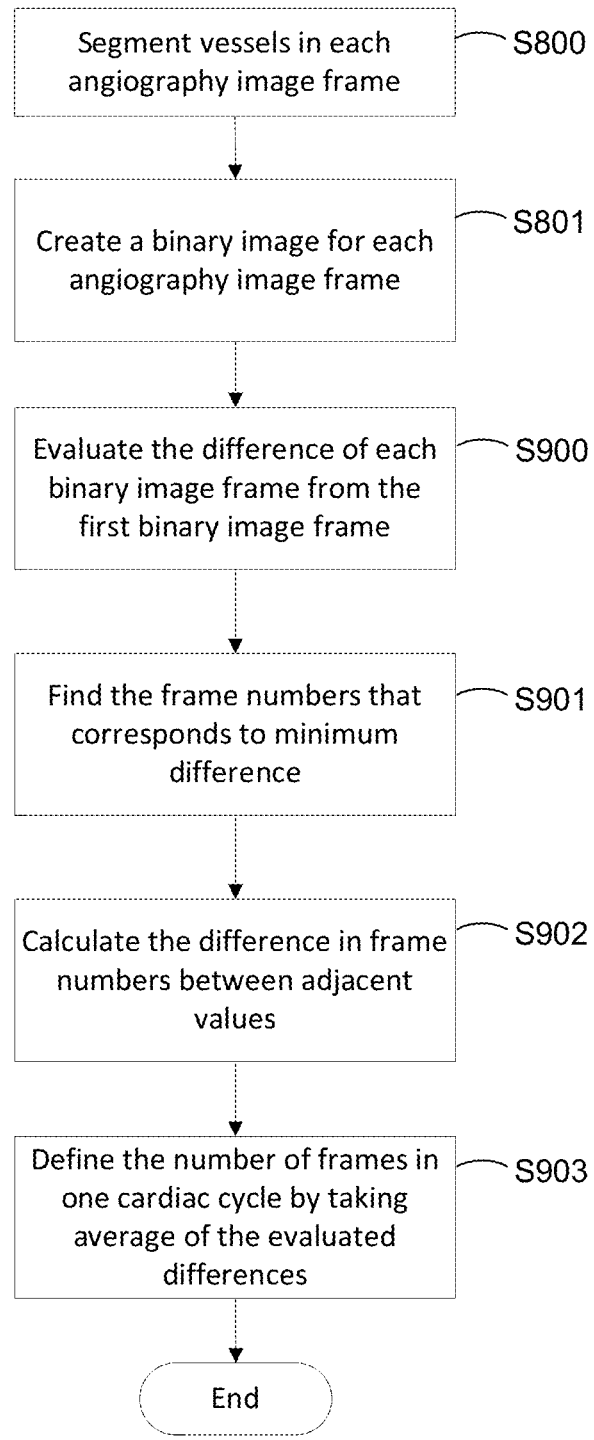
FIG. 15 is a flowchart illustrating various steps for estimating cardiac cycle in accordance with one or more aspects of the present disclosure.

FIG. 15 is a flowchart illustrating the various steps for estimating cardiac cycle. The first step S800 is the same as the first step in FIG. 12 of segmenting vessels in each angiography image frame and the binary image (bw data) that shows the segmented vessel for each frame is generated in step S801. If the cardiac motion has already been evaluated, steps S800 and S801 may be skipped in the process of estimating cardiac cycle and the information from the cardiac motion evaluation process may be used. Then, the system evaluates the absolute difference of each frame of bw data from the first frame of bw data in step S900. Then, the system finds the frame number(s) that correspond to the minimum difference in cardiac motion in step S901. At this step, 0, which is the absolute difference of the first frame, is not considered as the minimum difference. If a user prefers, the system may search the frame number(s) that correspond to not only the minimum difference, but also the second or more minimum differences. Once all the frame number(s) are found, the selected frame number(s) are sorted in ascending order and frame number 1 is added at the beginning of this series of numbers. Then, the difference(s) in frame numbers between adjacent sorted values is calculated in step S902. This difference is defined as number of frames in one cardiac cycle. If there are multiple differences, the average of the difference is considered as a number of frames in one cardiac cycle in step S903.

Figure 16:
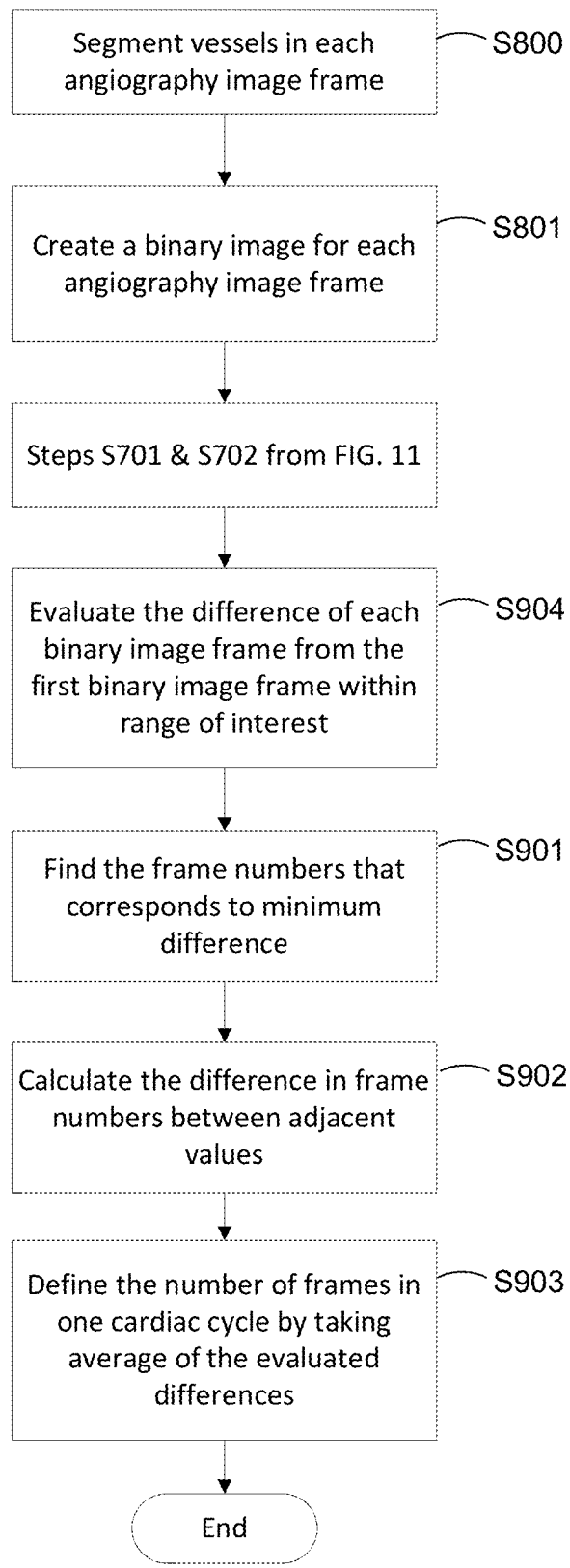
FIG. 16 is a flowchart illustrating various steps for estimating cardiac cycle in accordance with one or more aspects of the present disclosure.

The estimation process may be further improved if the range of interest is determined as illustrated in the following steps of the flowchart of FIG. 16. If the range of interest is already determined by evaluating the cardiac motion as described above, the system can evaluate the absolute difference of each frame from the first frame within the range of interest in step S904. This process focuses only on the area where the intravascular imaging is obtained and may eliminate any unnecessary structures such as ribs and diaphragm by way of example. The other steps in FIG. 16 are not repeated herein because they are similar to steps from FIGS. 11, 12 and 15.

Figure 17:
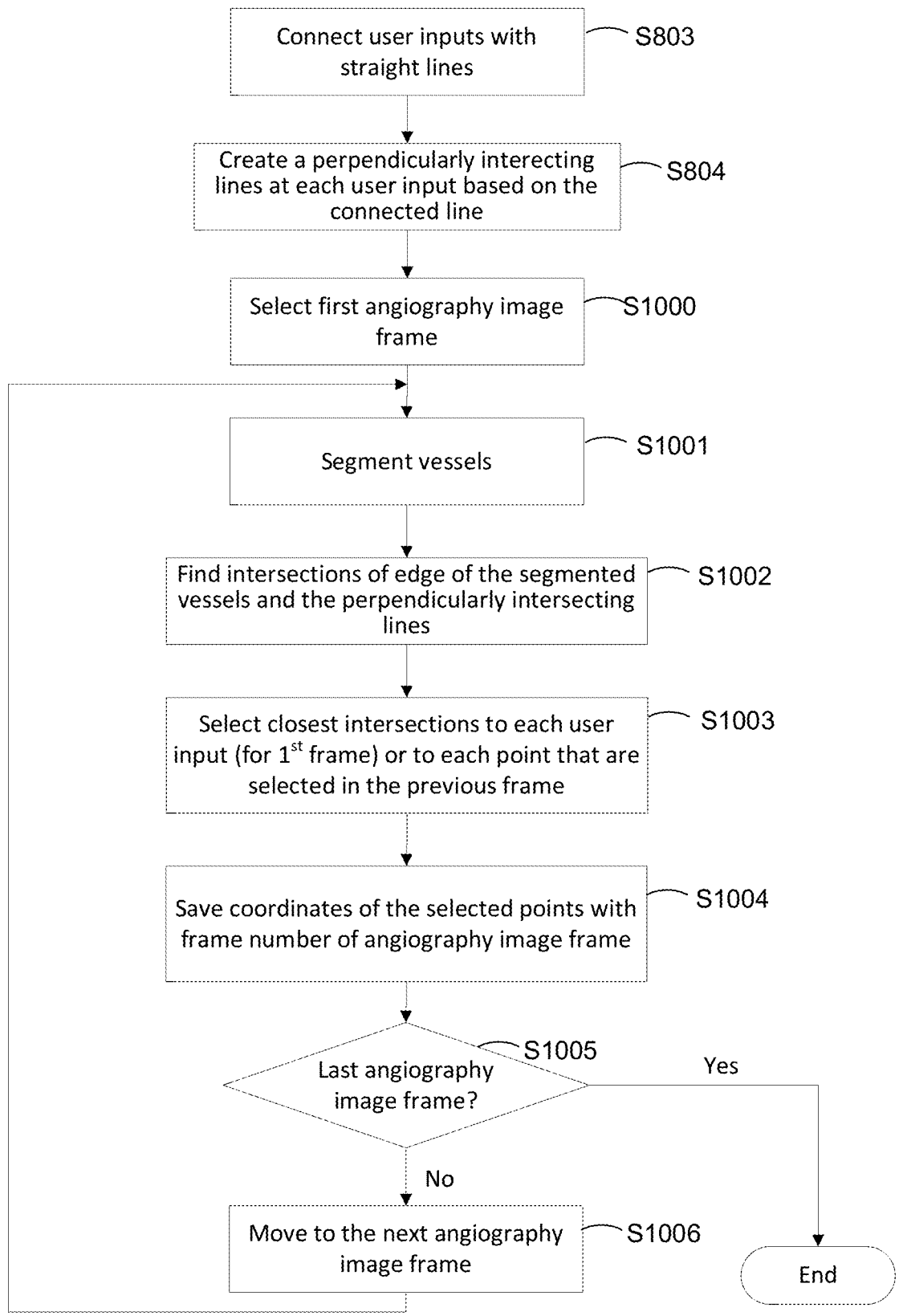
FIG. 17 is a flowchart illustrating another method for estimating cardiac cycle in accordance with one or more aspects of the present disclosure.
Figure 18:
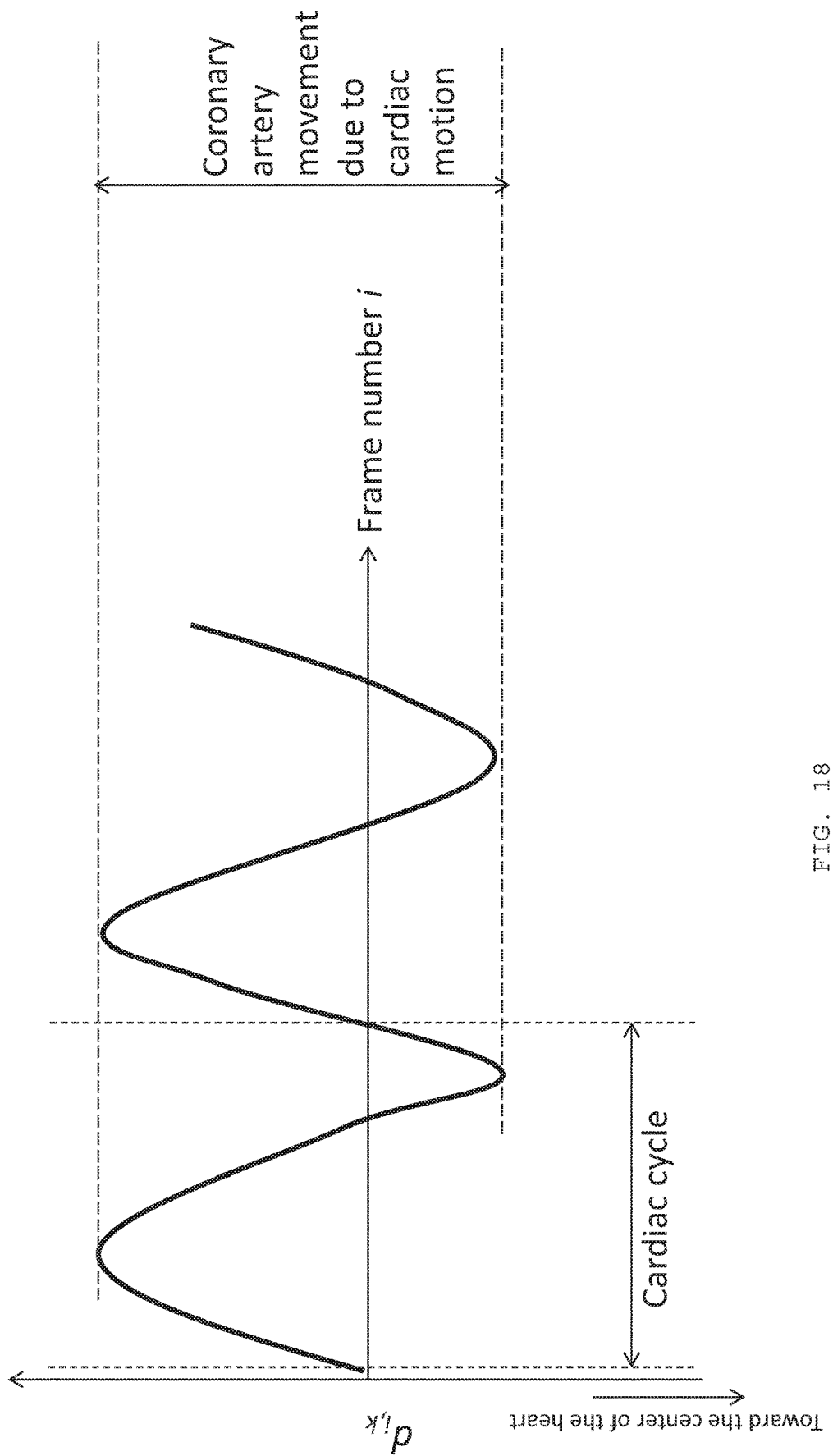
FIG. 18 is a graph illustrating coronary artery movement due to cardiac motion in accordance with one or more aspects of the present disclosure.

In another embodiment of the present disclosure, a second method for estimating the cardiac cycle is discussed with reference to FIGS. 17 and 18. In this embodiment, points that are close to the user inputs are tracked throughout the angiography image frame, and the cardiac cycle is estimated by evaluating movement of the tracked points with its moving directions. FIG. 17 is a flowchart illustrating various steps for selecting and the tracking the points. After the system obtains user inputs on one angiography image frame or on multiple image frames, the system connects the user inputs in step S803. In step S804, the system generates perpendicular lines at each user input that are connected to form a connected line. In step S1000, the system selects the first angiography image frame and segments vessels in the frame in step S1001. The segmentation in step S1001 may be performed in the same way as step S800 in FIG. 12. Then, intersections of the edge of the segmented vessels and the perpendicular lines are searched in step S1002. From these intersections, the closest points to each user input are selected in step S1003 and their coordinates are saved to the system with the frame number of the angiography image frame in step S1004. The coordinates of these points are denoted as $(x_{k,i}, y_{k,i})$, where i refers to the frame number and k (1–m) refers to the order of user inputs ($ui_1$ to $ui_m$). Then the next angiography image frame is selected in step S1006 and the same steps are repeated until the last angiography image frame is processed. If it is determined in step S1005 that the last angiography image frame has been processed the process ends. For any angiography image frame that is not the first angiography image frame at step S1003, the system selects the closest points to the points that were selected in the previous frame. Alternatively at step S1003, the system may select two closest points on both sides of the vessel, and the system calculates a midpoint and saves the coordinate of the midpoint at step S1004 for each user input or each point that is selected in the previous frame.

After this process, for each k, the movement of the points $d_{i,k}$ from the first frame is evaluated:

$$d_{i,k} = \|(x_{k,i}, y_{k,i}) - x_{k,1}, y_{k,1})\| (i \geq 2)$$

If the movement is toward the center of the heart, the sign of this value is changed to negative. If a user prefers, the movement of the opposite direction, i.e., outward from the center of the heart, can be treated as a negative value. To define the direction, the system can assume that the center of the image is close to the center of the heart, or the system can request a user to provide a user input to define the center of the heart on one automatically-selected angiography image frame. For a certain k, if all $d_{i,k}$ values are positive or negative, the system can identify the cardiac cycle by searching a frame number whose $d_{i,k}$ is close to zero. If not, the system can identify the cardiac cycle by searching a frame number whose $d_{i,k}$ is close to zero after $d_{i,k}$ value goes to positive and negative, or vice versa as shown in the graph of FIG. 18. After evaluating the number of frames in one cardiac cycle for each k, the system can calculate an average number of frames and define it as the number of frames in one cardiac cycle for the angiography data. The evaluation of $d_{i,k}$ can be used for evaluation of cardiac motion. As shown in FIG. 18, for each k, the difference between the maximum and minimum values of $d_{i,k}$ should correspond to the movement of the coronary artery at user input $ui_k$, and the system can use this information to evaluate CMx and CMy.

The aforementioned method for cardiac motion and cardiac cycle estimation can also be utilized for different processes in which the ECG signal or cardiac phase information obtained from the ECG signal is used. For example, in step S202, in another embodiment, the system may use cardiac phase information obtained from the aforementioned method, instead of using ECG signals, to select a frame without contrast media at the same cardiac phase. In another example, in step S108 or S116, cardiac phase information obtained from the aforementioned method may be saved with the angiography frames. Here the ECG device 60 does not need to be included, or at least does not need to be used for the co-registration process. Also, if the ECG device 60 is used with the angiography system 20, the estimation results may be utilized from the aforementioned method in a situation where the ECG signals are not synchronized with the angiography frames or the cardiac phase information from the ECG signals is not associated with each of the angiography frames.

In step S804, the system generates perpendicular lines 414-417, for estimating cardiac motion, at each user input that are connected to form a connected line. But in embodiments of the present disclosure, the lines for estimating cardiac motion may not necessarily be perpendicular to the line segments of the connected line. In one embodiment of the present disclosure, the system may generate lines intersecting at a certain angle, but not perpendicular to, the line segment connecting user inputs.

The generated lines may not necessarily be perpendicular to the longitudinal direction of the vessel, in a case that the vessel has a large curvature and a line segment connecting the user input points are not along the longitudinal direction of the vessel.

In another embodiment, the system may generate lines intersecting a curved line along a longitudinal direction of the vessel, instead of using the connected line. The curved line may be generated from Spline interpolation processing based on multiple user inputs.

As described above, in step S700, the imaging system 10 or the image processor 40 causes the monitor 50 to display multiple angiography frames for receiving user inputs in these frames. In embodiments of the present disclosure, one or more frames of one or more specific cardiac phases, evaluated from the cardiac motion, are identified and displayed. In one embodiment, the imaging system 10 may identify or select one or more angiography frames based on the cardiac cycle estimation as described with reference to FIGS. 15-18. In one embodiment, the imaging system 10 selects and causes the monitor 50 to display one or more angiography frames of the same cardiac phase as the pre-selected frame for receiving user input points for cardiac cycle estimation. By receiving and utilizing user inputs in multiple frames of the same cardiac phase, the accuracy of marker detection is improved.

In another embodiment, the imaging system 10 selects and causes the monitor 50 to display one or more angiography frames of different cardiac phases than the pre-selected frame. The imaging system 10 may select and cause the monitor 50 to display one or more frames. The one or more frames may include frames at peaks of $d_{i,k}$ (where the distance is at its local maximum and at its local minimum) of one cardiac cycle as shown in FIG. 18. By receiving and utilizing user inputs in these frames, the accuracy of marker detection is improved. The imaging system 10 may select a frame of which $d_{i,k}$ has bigger absolute difference from the one of the pre-selected frame. The one or more frames may include a frame at the highest velocity of the coronary artery movement $d'_{i,k}$, i.e., the gradient value of the cycle curve that is shown in FIG. 18 is at its maximum or minimum. By receiving and utilizing user inputs in the frame, the accuracy of marker detection is improved.

In aforementioned embodiments multiple (perpendicular) lines are determined at user inputs to evaluate cardiac motion, but at least for estimating the cardiac phase information, the imaging system 10 may evaluate only one position of the vessel region in the multiple angiographic image frames. The one position can be predetermined by the imaging system 10 or can be selected by a user.

Figure 19:
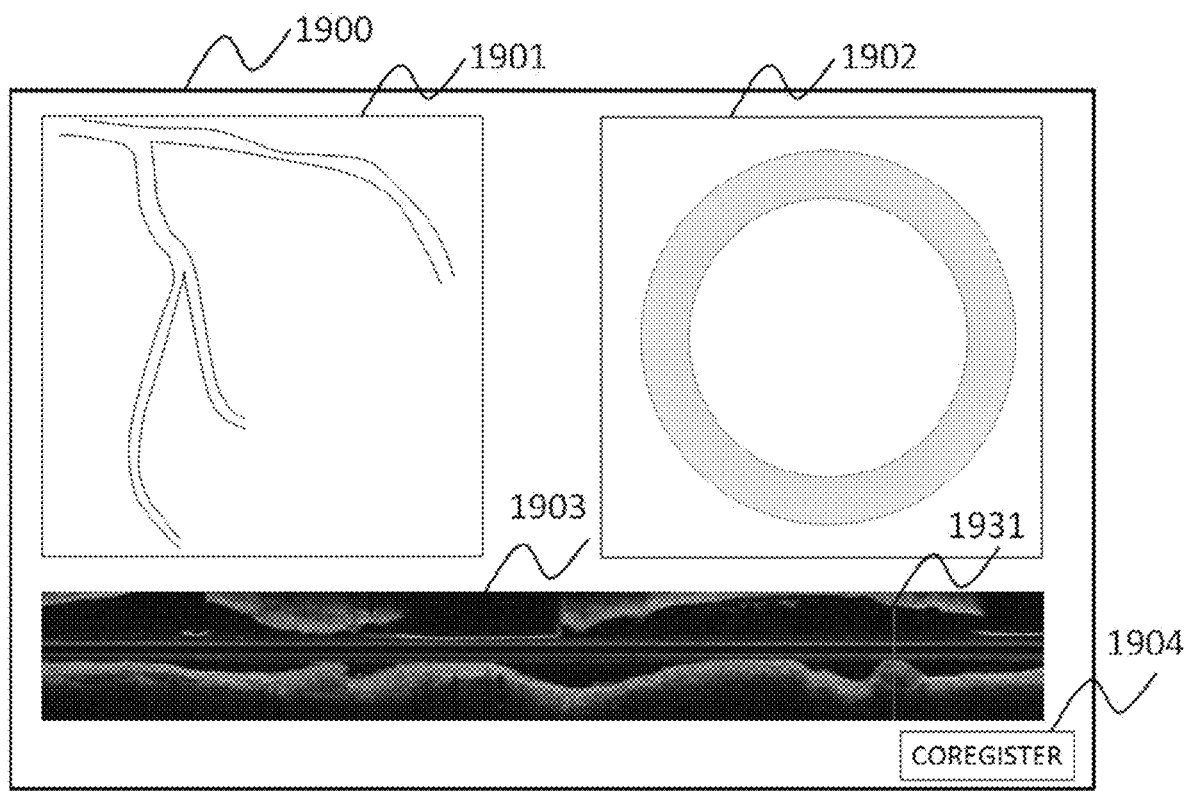
FIG. 19 is a diagram illustrating a graphical user interface for displaying an intravascular image and an angiography image in accordance with one or more aspects of the present disclosure.
Figure 20:
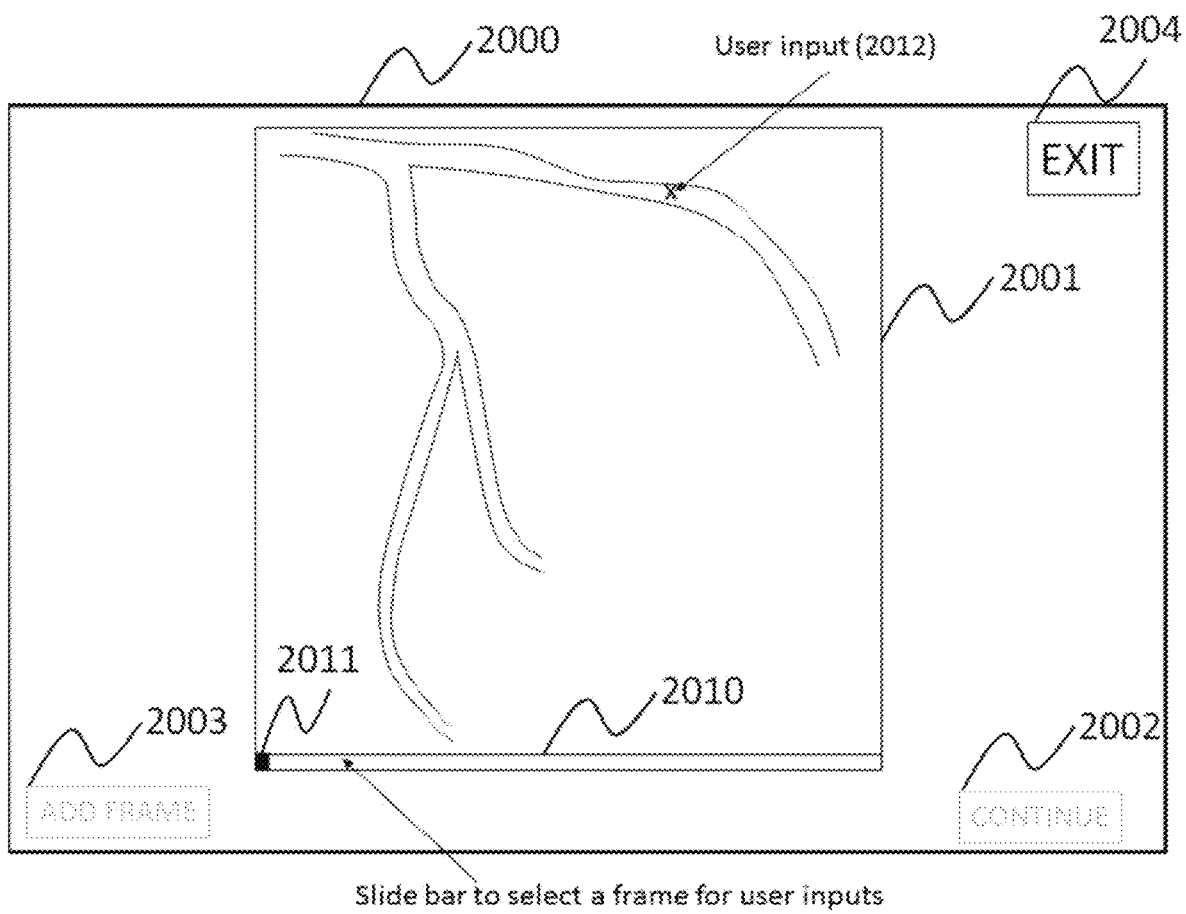
FIG. 20 is a diagram illustrating a graphical user interface for receiving user inputs for co-registration in accordance with one or more aspects of the present disclosure.
Figure 21:
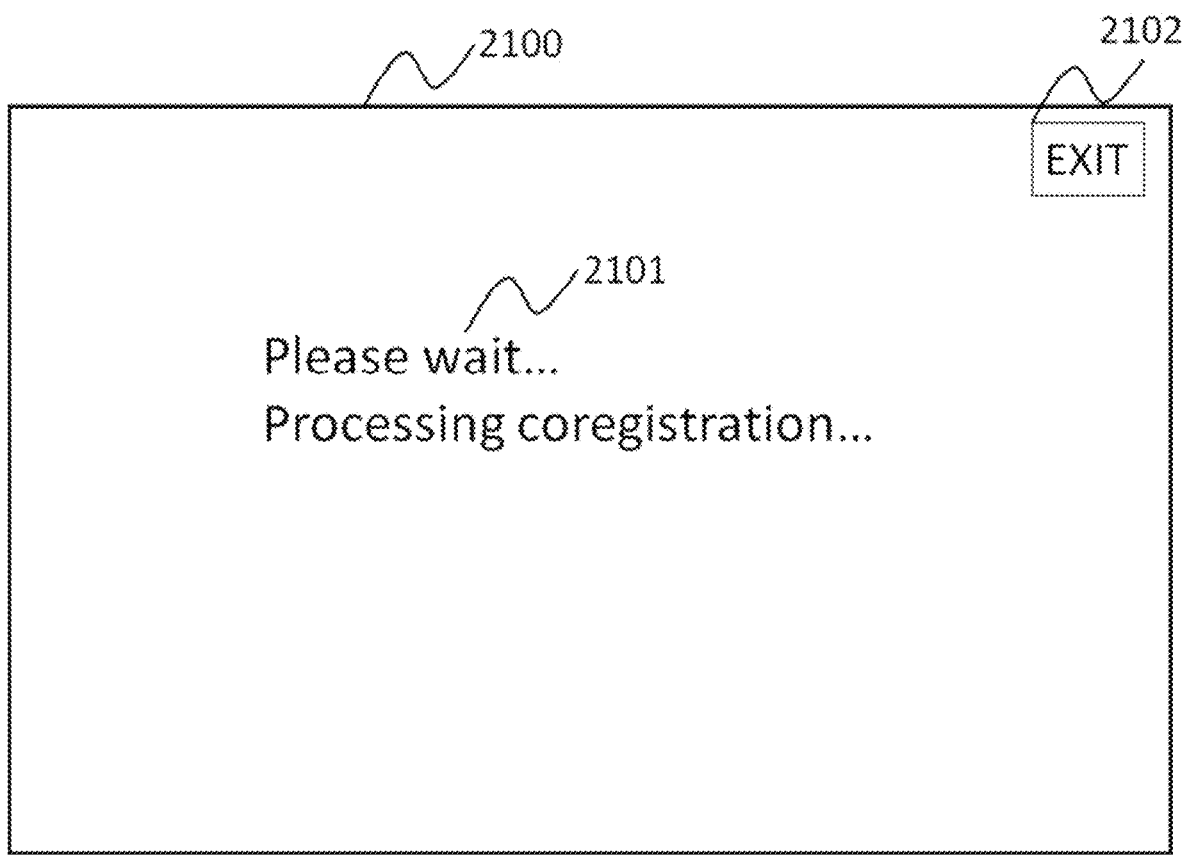
FIG. 21 is a diagram illustrating a graphical user interface for displaying information while the co-registration processing is being performed, in accordance with one or more aspects of the present disclosure.

In another embodiment, the system 10 displays on the display 50 (or, the image processor 40 causes the display 50 to display) multiple GUIs to navigate a user during the co-registration process. After step S20 in FIG. 2, the system displays a GUI to show the acquired angiography image and the intravascular image together. The example GUI 1900 is shown in FIG. 19. The GUI 1900 includes an area 1901 to display an angiography image frame, an area 1902 to display an intravascular image frame, and an area 1903 to display a longitudinal view of the vessel, and the "COREGISTER" button 1904. In this GUI 1900, a user can (a user uses an input device, for example, a mouse device, keyboard or a touch panel display to) move a line 1931, superimposed on the longitudinal view, in a horizontal direction of the GUI 1900, to select and display in the area 1902 an intravascular image, corresponding to the position of the line 1931. A co-registration process can be initiated by a user, for example, by clicking "COREGISTER" button 1904 in FIG. 19, and then, the system 10 displays the next GUI to obtain user inputs. The example GUI 2000 is shown in FIG. 20. The GUI includes an area 2001 to display an angiography image frame, a slide bar 2010 with a cursor 2011, a "CONTINUE" button 2002, an "ADD FRAME" button 2003, and an "EXIT" button 2004. In this GUI 2000, the system 10 automatically selects and displays the first angiography image frame acquired during the intravascular imaging pullback. By displaying the first angiography image frame during the pullback, a user may identify the initial location of the intravascular imaging acquisition relatively easily, which helps a user define the distal region of the intravascular imaging pullback in the vessel. It also helps the system to identify the radiopaque marker location on the first frame. In one embodiment, the first angiography image can be an angiography image acquired right before or right after the pullback is started, or any angiography image in which initial location of the intravascular imaging catheter 38 is displayed. In one embodiment, if a user prefers, the user may change the angiography image frame, the area 2001 to place user inputs, for example, by moving the cursor 2011 in the slide bar 2010 so that the system 10 displays an angiography image frame corresponding to the position of the cursor 2011 of the slide bar 2010. In this example GUI 2000, a user places a first user input 2012 on a displayed angiography image frame by clicking a location in the displayed angiography image frame 2001. In a case when only one user input 2012 is placed on the angiography image frame, both the "CONTINUE" button 2002 and the "ADD FRAME" button 2003 are disabled by the system 10. In a case when at least two user inputs are placed by a user, both buttons are activated by the system 10. If the "CONTINUE" button 2002 is selected by a user, the system 10 performs the co-registration processes S30-S50 in FIG. 2. During the processes, the system 10 displays another GUI. The example GUI 2100 is shown in FIG. 21. The GUI 2100 includes a message 2101 for letting a user know the processes are on-going, and an "EXIT" button 2102. While the system 10 performs processes, if a user wants to quit the co-registration process for any reasons, a user can click on the "EXIT" button 2102. Once the "EXIT" button 2102 is clicked, the system stops the co-registration processes and returns to the GUI 1900. Before returning to the GUI 1900, the system 2100 can display an additional window with a button, to double-check with a user whether to stop co-registration processes. "EXIT" buttons in FIGS. 20, 22, 23, and 25 also have the same function as the "EXIT" button 2102 as described here.

Figure 22:
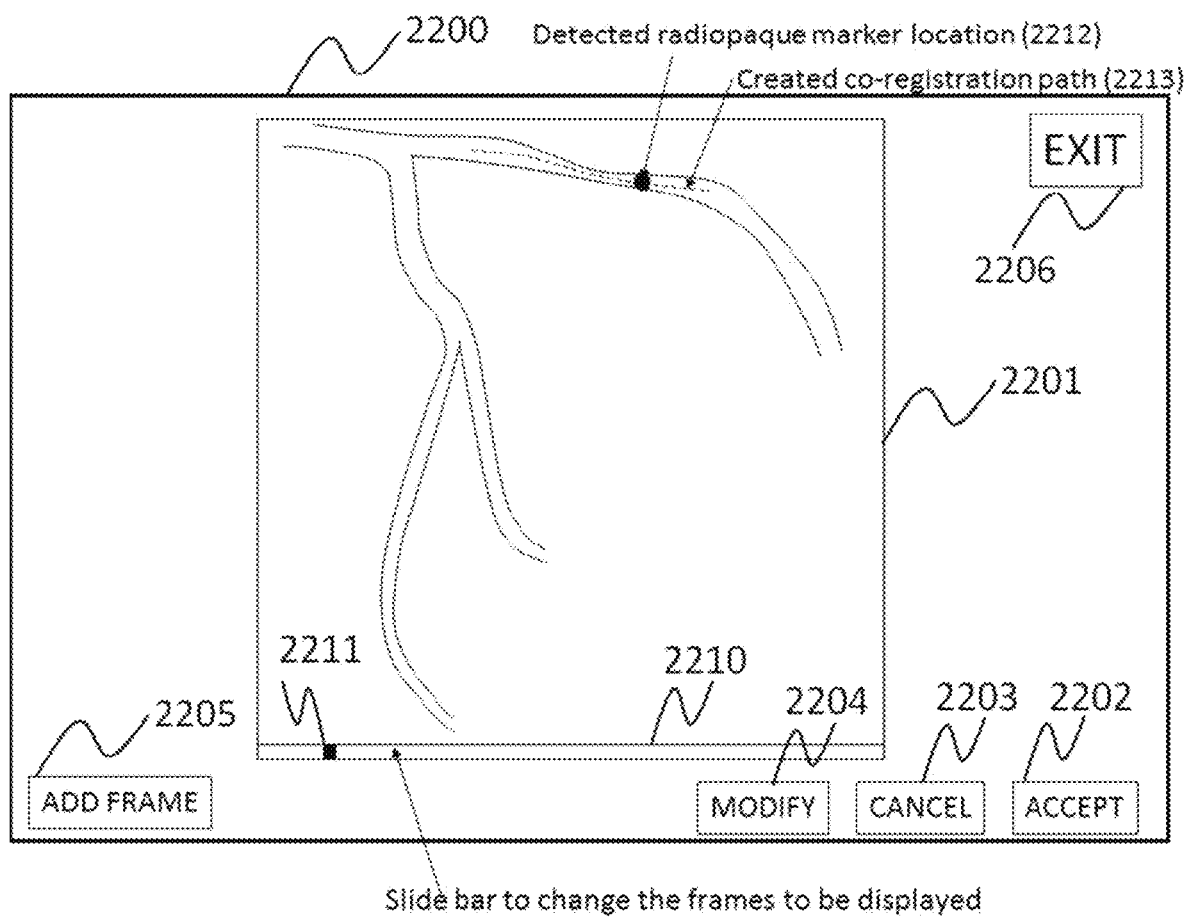
FIG. 22 is a diagram illustrating a graphical user interface for displaying a co-registration result for user confirmation, in accordance with one or more aspects of the present disclosure.

In one embodiment, a user can check the result of detection before step S60 in FIG. 2. Once the co-registration processes S30-S50 are completed, the system 10 displays the result of the detection of the radiopaque marker and asks a user whether the result is acceptable or not. FIG. 22 includes an example GUI 2200 for this stage. The GUI 2200 includes an area to display an angiography image, a slide bar 2210 with a cursor 2211, an "ACCEPT" button 2202, a "CANCEL" button 2203, a "MODIFY" button 2204, an "ADD FRAME" button 2205, and an "EXIT" button 2206. On the displayed angiography image frame, the system 10 overlays an indicator 2212 indicating a radiopaque marker location detected in the co-registration process, and a line 2213 indicating the co-registration path created in the co-registration process. The indicator 2212 can be an arrow to point out the radiopaque marker location. If a user prefers, the system 10 can overlay the acquisition location of the intravascular imaging frame instead of the detected radiopaque marker location in the case that there is a certain distance between the radiopaque marker and the acquisition location, i.e., the distal optics location, on the intravascular imaging catheter. The user can move the cursor 2211 to change the angiography frame displayed in the area 2201 to check if the detected radiopaque marker location 2212 is acceptable in any angiography image frame during the pullback. The GUI 2200 is displayed for user confirmation of the co-registration result including radiopaque marker detection result. With the GUI 2200, the system 10 makes a determination or recognizes a user decision, as to whether the system 10 displays the co-registration results or not.

Figure 23:
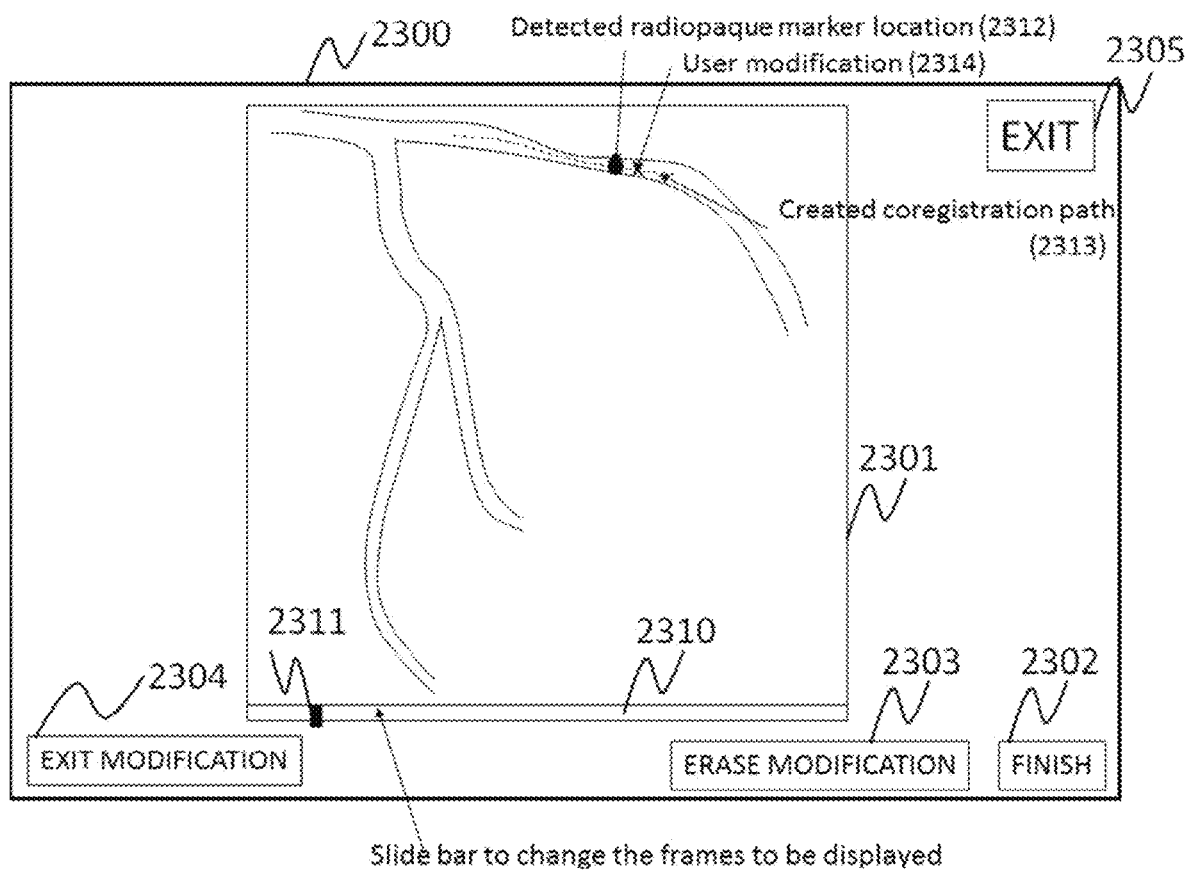
FIG. 23 is a diagram illustrating a graphical user interface for receiving a user modification in accordance with one or more aspects of the present disclosure.

The system 10 selects to display a different GUI based on the check result by a user. If a user accepts the result, e.g., a user clicks the "ACCEPT" 2202 button, and in response to the click the system 10 displays a GUI that has an angiography image with the co-registration result including the detected marker locations. The example GUI is the GUI 200 as shown in FIG. 10. In this GUI 200, as described before, the co-registration path 210 and the artificial indicator 212 that indicates the acquisition location of the corresponding intravascular imaging frame are overlaid on the angiography image frame 202. If a user does not accept the result, e.g., a user clicks the "CANCEL" button 2203, the system 10 displays a GUI without the co-registration result, i.e., no information is overlaid on the angiography image frame. The example GUI is the GUI 1900. At this stage, the "COREGISTER" button on FIG. 19 can be disabled or removed. If a user would like to modify the detection result frame-by-frame, a user clicks the "MODIFY" button 2204 and the system 10 navigates a user with different GUIs. The example GUI 2300 is shown in FIG. 23. The GUI 2300 includes an area 2301 to display an angiography image frame, a slide bar 2310 with a cursor 2311, a "FINISH" button 2302, an "ERASE MODIFICATION" button 2303, an "EXIT MODIFICATION" button 2304, and an "EXIT" button 2305. In this GUI 2300, the system 10 displays the angiography image frames with an indicator 2312 indicating a detected radiopaque marker location and with a line 2313 indicating a co-registration path. For the GUI 2300, the system 10 also selects and initially displays the angiography image frame that a user reviewed when "MODIFY" button is clicked at the previous GUI 2200, and the cursor 2311 is initially positioned in accordance with the displayed angiography image frame in the area 2301. A user may change the frame to be displayed in the area 2301 by moving the cursor 2311 of the slide bar 2310, as one example way. The "FINISH" button 2302 and the "ERASE MODIFICATION" button 2303 are initially disabled by the system 10, but once a user clicks the actual radiopaque marker location on the angiography image frame to input a location of a user modification 2314, both the "FINISH" button 2302 and the "ERASE MODIFICATION" 2303 button are activated by the system 10. In response to a receipt of the user modification 2314, the system 10 stores in a memory of the system 10 information of the location of the user modification 2314 in the displayed angiography image frame with its frame number or its identification information. If a user clicks the "ERASE MODIFICATION" button 2304, the system 10 erases or removes the user modification 2314 from the displayed GUI 2300 and the location of the user modification 2314 from the memory. When a user finishes modifying the detected marker location, a user clicks the "FINISH" button 2302. Once the "FINISH" button 2302 is clicked, the system 10 recalculates the acquisition location of the intravascular image frames that are affected by the user modification 2314. If a user wants to quit modification process, a user can click the "EXIT MODIFICATION" button 2304, and the system can show the GUI 2200. If a user prefers, the system 10 can directly display the final result GUI 200 in FIG. 10 or display the GUI 1900 after the "EXIT MODIFICATION" button 2304 is clicked. The "EXIT MODIFICATION" button 2304 is activated whenever the system 10 displays the GUI 2300.

Figure 24:
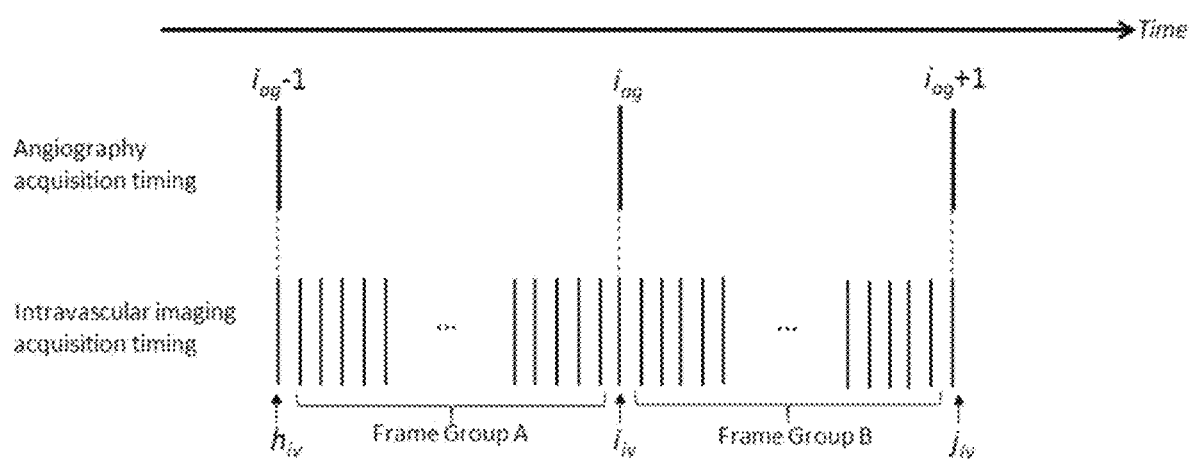
FIG. 24 illustrates a relationship between angiography acquisition timing an intravascular imaging acquisition timing in accordance with one or more aspects of the present disclosure.

In this modification process, as mentioned above, when a user clicks the "FINISH" button 2302, the system 10 recalculates the acquisition location of the intravascular image frames that are affected by the user modification 2314. In other words, co-registration is performed again for intravascular image frames acquired in a certain time range from a time when the angiography image frame is acquired. The system 10 displays the GUI 2100 when the recalculation processing is being performed. Referring to FIG. 24, assume that a user modifies the detected result on $i_{ag}$-th angiography image frame and that ($i_{ag}$−1)-th, $i_{ag}$-th, and ($i_{ag}$+1)-th angiography image frames are acquired at the same time when $h_{iv}$-th, $i_{iv}$-th, and $j_{iv}$-th intravascular image frames are acquired, respectively. When the acquisition location of the $i_{ag}$-th angiography image frame is modified by a user, this user modification affects the calculated acquisition locations for the ($h_{iv}$+1)-th to ($i_{iv}$−1)-th (Frame group A in FIG. 24) and ($i_{iv}$+1)-th to ($j_{iv}$−1)-th (Frame group B in FIG. 24) intravascular imaging frames. As described before, the system 10 calculates acquisition locations for the intravascular imaging frames in Frame Group A based on the detection result on ($i_{ag}$−1)-th and the modified result on $i_{ag}$-th angiography image frames, acquisition locations for the intravascular imaging frames in and Frame Group B based on the modified result on $i_{ag}$-th and the detection result on ($i_{ag}$+1)-th angiography image frames.

In another embodiment, The system 10 provides a user with different methods for receiving user inputs to obtain better co-registration result. For example, one method requires a user to place user inputs on only one angiography image frames. The other method requires a user to place user inputs on multiple angiography image frames. The number of user inputs per frame can be one or multiple. In this description, Method 1 is defined as one angiography image frame with multiple user inputs/frame, Method 2 is defined as multiple angiography image frames with one user inputs/frame, and Method 3 is defined as multiple angiography image frames with multiple user inputs/frame. Referring back to FIG. 20 or FIG. 22, the GUI has the "ADD FRAME" button 2003 or 2205. In one embodiment, the co-registration process starts with Method 1, and if a user prefers, a user can provide more user inputs on the other frames by clicking the "ADD FRAME" button 2003 or 2205. If a user clicks the button 2003, the initial co-registration process is performed with either Method 2 or Method 3. If a user clicks the button 2205, the system re-performs co-registration process with Method 2 or Method 3. The selection of Method 2 or Method 3 can be done automatically by the system, can be done by setting a default beforehand based on user preference information stored in a memory of the system 10, or can be done at each intravascular imaging pullback procedure by a user.

Figure 25:
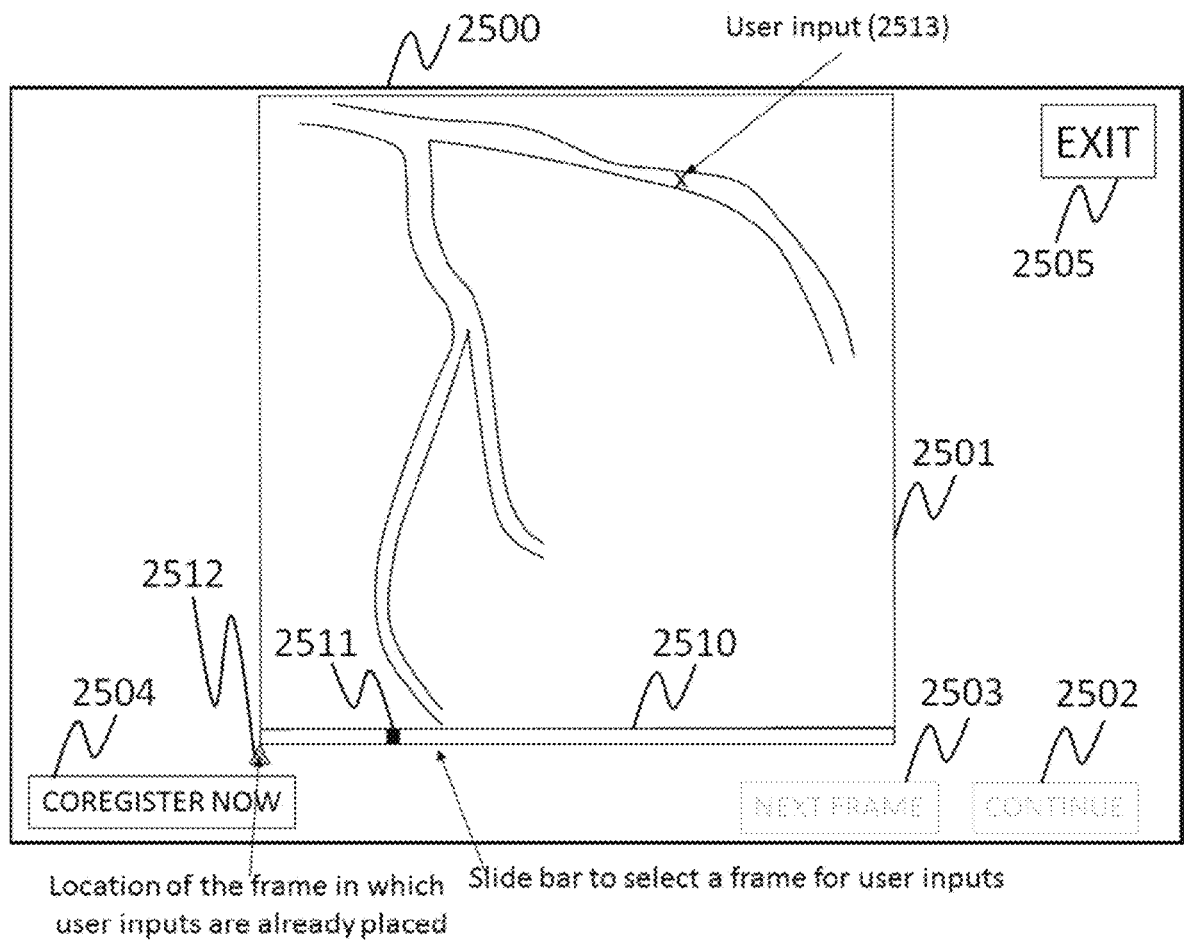
FIG. 25 is a diagram illustrating another graphical user interface for receiving user inputs for co-registration in accordance with one or more aspects of the present disclosure.

Once the "ADD FRAME" button 2003 or the button 2205 is clicked, the system 10 displays another GUI to obtain more user inputs. The example GUI 2500 is shown in FIG. 25. In this example, the system selects to perform co-registration with Method 3. The GUI 2500 includes an area 2501 to display an angiography image frame, a slider bar 2510 with a first cursor 2511 and a marker 2512, a "CONTINUE" button 2502, a "NEXT FRAME" button 2503, a "COREGISTER NOW" button 2504, an "EXIT" button 2505. The cursor 2511 is movable by a user, may be a rectangular shape, and its position is corresponding to an angiography image frame displayed in the area 2501. The marker 2512 indicates a location of a frame in which user inputs are already placed. The marker 2512 may be a triangular shape, which may be visually different from the cursor 2511, and may be positioned under the slider bar 2510, while the cursor 2511 may be positioned in the slide bar 2510. In the GUI 2500, a user places the first user input 2513 on a new angiography image frame displayed in the area 2501. The angiography image frame for a user to provide more user inputs can be selected automatically by the system with or without the estimated cardiac cycle information or can be manually selected by a user with a slide bar, as described before. The triangle marker 2512 indicates the angiography image frame location in which a user already provides user inputs. In this example GUI 2500, as same as previously described, since only one user input is placed on the angiography image frame, the "CONTINUE" button 2502 and the "NEXT FRAME" button 2503 are disabled. Both buttons are activated once a user places two or more user inputs on the displayed angiography image frame. Once a user clicks the "NEXT FRAME" button 2503, the system automatically displays the next angiography image frame out of the angiography image frames selected by the system 10, with the same GUI shown in FIG. 25. When the system displays the last angiography image frame out of the frames selected by the system 10, "NEXT FRAME" button can be disabled or will not be available on the GUI 2500. In one embodiment, the system 10 selects one or more angiography image frames of the same cardiac phase based on cardiac cycle information, and the system 10 can display, along the slider bar 2510, one or more markers which is/are visually different from the marker 2512, at position(s) corresponding to the selected one or more frames. The cardiac cycle information can be obtained from the ECG 60, or the image processing of the angiography image frames as shown in FIG. 12. In order to utilize the image processing, in one embodiment, the image processing can be started in response to a click of the "ADD FRAME" button 2003 in the GUI 2000. In this case the image processing system 10 can initially displays one of the selected angiography image frame(s) in the GUI 2500.

If Method 2 is selected in the GUI 2500, the "NEXT FRAME" button 2503 is removed. Since only one user input is required and sufficient per frame, in response to one user input which a user places, the system can automatically display a next angiography image frame in the GUI 2500.

For both Method 2 and Method 3, an additional button that allows a user to go back to the previous frame (e.g., "PREVIOUS FRAME" button) can be displayed in the GUI 2500. In addition, if a user prefers, the system 10 can display the user inputs that are provided on the other frame(s), on the currently displayed angiography image frame, as a reference for a user. If a user clicks the "CONTINUE" button 2502, the system 10 performs co-registration process using all the user inputs information that is given on all the angiography image frames including the currently-displayed angiography image frame, even if a user has not finished placing user inputs on all the angiography image frames that are selected to be used. If a user clicks the "COREGISTER NOW" button 2504, the system 10 performs co-registration process using all the user inputs information that is given on all the frames except the currently-displayed angiography image frame. When the "CONTINUE" button 2502 or the "COREGISTER NOW" button 2504 is clicked by a user, the system 10 displays the GUI 2100 to let a user know that the system 10 is performing co-registration process. In this GUI 2100, "EXIT" button is also displayed and available all the time to allow a user to stop co-registration process and return to the GUI 1900.

In another embodiment, a user can select a method to provide user inputs before co-registration process starts. Once a user clicks the "COREGISTER" button 1904 in the GUI 1900, the system 10 can display another GUI for a user to select a method (Methods 1, 2 or 3, as an example). Based on the user's selection, the system 10 determines the next GUI and performs co-registration process. For example, the system displays the GUI 2000 if Method 1 is selected, displays the GUI 2500 without the "NEXT FRAME" button 2503 if Method 2 is selected, and displays the GUI 2500 with the "NEXT FRAME" button 2503 if Method 3 is selected.

In another embodiment, since the system 10 has an ability to evaluate the reliability of co-registration, if the evaluated reliability is lower than a threshold, the system can display a notification message to a user and can automatically go back to the original GUI 1900. If a user prefers to see the result even if the evaluated reliability is lower than the threshold, the system 10 can display the result on GUI 200 with an alert. The alert can be a text message or can be a symbol. The threshold for the reliability can be determined by the system or can be modified by a user prior to the procedure or during the procedure.

Figure 26:
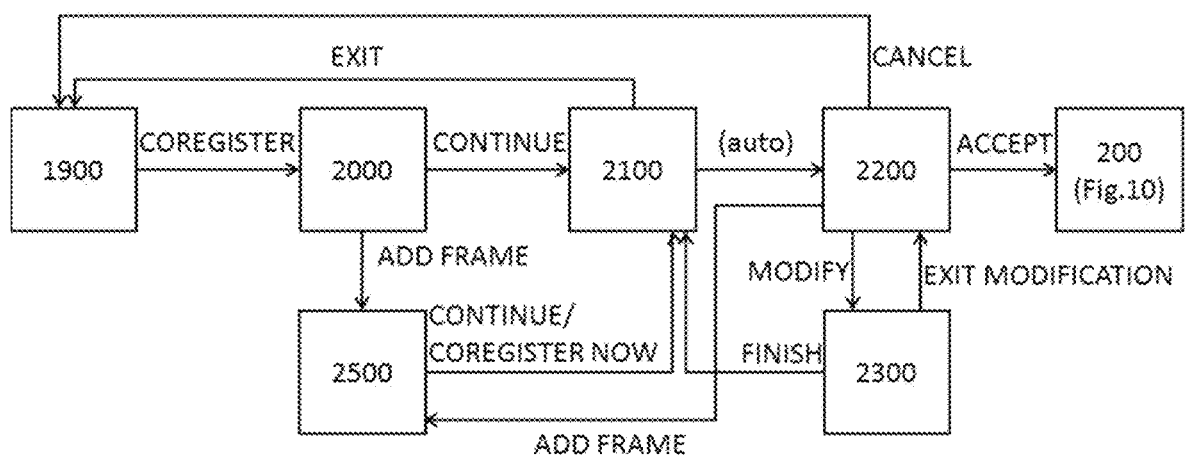
FIG. 26 illustrates a schematic diagram for screen transition in accordance with one or more aspects of the present disclosure.

FIG. 26 illustrates screen transition according to one embodiment of the present invention. The image processor 40 causes the display 50 to display the GUI 2000 in a case that the displayed "COREGISTER" button 1904 in the displayed GUI 1900 is clicked.

The image processor 40 causes the display 50 to display the GUI 2100 in a case that the displayed "CONTINUE" button 2002 in the displayed GUI 2000 is clicked, to display the GUI 2500 in a case that the displayed "ADD FRAME" button 2003 is clicked, and to display the GUI 1900 in a case that the displayed "EXIT" button 2004 is clicked.

The image processor 40 causes the display 50 to automatically display the GUI 2200 in response to a completion of the co-registration processing as shown in FIG. 2, and to display the GUI 1900 in a case that the displayed "EXIT" button 2102 in the displayed GUI 2100 is clicked.

The image processor 40 causes the display 50 to display the GUI 200 as shown in FIG. 10 in a case that the displayed "ACCEPT" button 2202 in the displayed GUI 2200 is clicked, to display the GUI 1900 in a case that the displayed "CANCEL" button 2203 is clicked, to display the GUI 2300 in a case that the displayed "MODIFY" button 2204 is clicked, to display the GUI 2500 in a case that the displayed "ADD FRAME" button 2205 is clicked, and to display the GUI 1900 in a case that the displayed button "EXIT" 2206 is clicked The image processor 40 causes the display 50 to display the GUI 2100 in a case that the displayed "FINISH" button 2302 in the displayed GUI 2300 is clicked, to display the GUI 2200 in a case that the displayed "EXIT MODIFICATION" button 2304 is clicked, to display the GUI 1900 in a case that the displayed button "EXIT" 2305 is clicked, and to remove the user's modification of the detected marker location (if any) from the GUI 2300 in a case that the displayed button "ERASE MODIFICATION" 2303 is clicked.

The image processor 40 causes the display 50 to display the GUI 2100 in a case that one of the displayed "CONTINUE" button 2502 and the displayed "COREGISTER NOW" button 2504 in the displayed GUI 2500 is clicked, to display the GUI 1900 in a case that the displayed "EXIT" button 2505 is clicked, and to change the angiography image frame displayed in the area 2501 in the GUI 2500 in a case that the "NEXT FRAME" button 2503 is clicked or that a position of the cursor 2511 on the slide bar 2510 is changed, for example, by clicking at a certain location on the slide bar 2510 or by the cursor 2511 being moved by a user.

A button in the GUI 1900, 2000, 2100, 2200, 2300 or 2500 can be one of examples of an item for receiving a user instruction or input, and the button can be an icon, a hyperlink, or any kind of item for receiving user instruction or inputs. A combination of a slide bar and a movable cursor is displayed in the GUI 2200, 2300, or 2300, for a user to select an angiography image frame to be displayed, in other words the system 10 displays a different angiography image in response to a movement of the movable cursor, but the combination can be any item for receiving user instruction for selecting an angiography image frame to be displayed.

While the GUI 2100 is displayed, or in response to a user instruction to start co-registration process by clicking the button 2002, the system 10 can perform both the cardiac cycle/phase estimation and the co-registration process as described above. Thus, after the co-registration or the cardiac phase estimation is performed, the system 10 can display an angiography image frame of a specific cardiac phase, for receiving a user input in the GUI 2500.

Figure 27:
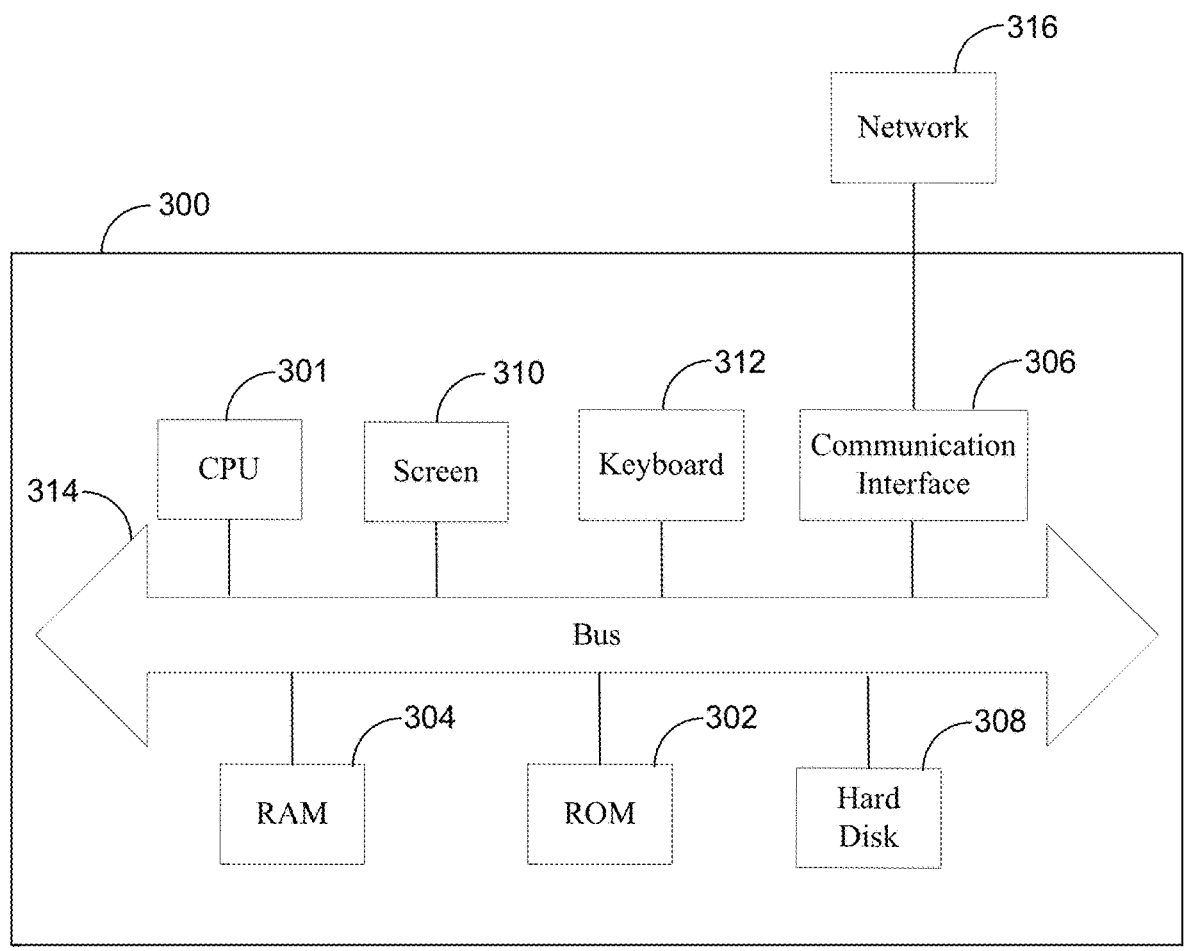
FIG. 27 illustrates a schematic diagram of an embodiment of a computer that may be used for generating a co-registration path in accordance with one or more aspects of the present disclosure.

FIG. 27 is an exemplary block diagram of a hardware configuration of the computer 34 of FIG. 1. However, the computer 300 may also be implemented in the angiography system 20 instead of the intravascular imaging system 30. In another embodiment of the present disclosure the computer 300 may be a stand-alone device encompassing the image processor 40 shown in FIG. 1.

The computer 300 include a central processing unit ("CPU") 301, a ROM 302, a RAM 304, a communication interface 306, a hard disk (and/or other storage device) 308, a display interface 310, an input device (for example, a mouse, keyboard or a touch panel) 312 and a BUS or other connection lines (e.g., connection line 314) between one or more of the aforementioned components as shown in FIG. 27. The computer 300 may include one or more combinations of the other aforementioned components. The CPU 301 is configured to read and perform computer-executable instructions stored in a storage medium. The computer-executable instructions may include those for the performance of the methods and/or calculations described herein. The computer 300 may include one or more additional processors in addition to CPU 301, and such processors, including the CPU 301, may be used for acquiring information from an intravascular imaging system, an angiography system, and EGC device to determine a co-registration path with an indicator representative of a position along the co-registration path where an intravascular image frame is acquired. The computer 300 may further include one or more processors connected via a network connection (e.g., via network 316). The CPU 301 and any additional processor being used by the computer 300 may be located in the same telecom network or in different telecom networks.

The I/O or communication interface 306 provides communication interfaces to input and output devices, which may include the two light source 33, a communication cable and a network (either wired or wireless), a keyboard, a mouse, a touch screen or monitor 50.

Any methods and/or data of the present disclosure, such as the methods for generating a co-registration path, may be stored on a computer-readable storage medium. A computer-readable and/or writable storage medium used commonly, such as, but not limited to, one or more of a hard disk (e.g., the hard disk 308, a magnetic disk, etc.), a flash memory, a CD, an optical disc (e.g., a compact disc ("CD") a digital versatile disc ("DVD"), a Blu-ray' disc, etc.), a magneto-optical disk, a random-access memory ("RAM") (such as the RAM 304), a DRAM, a read only memory ("ROM"), a storage of distributed computing systems, a memory card, or the like (e.g., other semiconductor memory, such as, but not limited to, a non-volatile memory card, a solid state drive, SRAM, etc.), an optional combination thereof, a server/database, etc. may be used to cause a processor, such as, the processor or CPU 301 of the aforementioned computer 300 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

The above described devices, systems, and methods can be implemented by supplying one or more computer-readable media having stored therein computer-executable instructions for realizing the above described operations to one or more computer devices that are configured to read the computer-executable instructions and execute them. In this case, the system or devices perform the operations of the above-described embodiments when executing the computer-executable instructions. Also, an operating system on the one or more systems or devices may implement the operations of the above described embodiments. Thus, the computer-executable instructions or the one or more computer-readable media storing the computer-executable instructions or the one or more computer-readable media storing the computer-executable instructions thereon constitute an embodiment.

While the above disclosure describes certain illustrative embodiments, the present disclosure is not limited to the above-described embodiments, and the following claims include various modifications and equivalent arrangements within their scope.

What is claimed is:

1. A method for processing an angiographic image, the method comprising:
   obtaining multiple angiographic image frames of a vessel region and multiple intravascular image frames acquired by an imaging catheter in the vessel region during pullback of the imaging catheter;
   detecting the vessel region in each of the multiple angiographic image frames;
   defining a direction intersecting a longitudinal direction of the vessel region;
   detecting motion of the vessel region based on the direction by evaluating positions of the vessel region in the multiple angiographic image frames;
   defining an area based on the detected motion and the detected vessel region;

detecting a marker of the imaging catheter disposed in the vessel region within the area, in at least one of the multiple angiography image frames; and performing co-registration between the multiple angiographic image frames and the multiple intravascular image frames, based on the detected marker.

2. The method of claim 1, wherein the vessel region is detected by obtaining a user input identifying a location of a coronary artery in which intravascular imaging pullback was performed on a graphical user interface.

3. The method of claim 1, wherein the vessel region is segmented by assigning a first predetermined value for areas of the vessel region in which contrast media is located and a second predetermined value for areas of the vessel region in which contrast media is not located.

4. The method of claim 3, further comprising:
generating a binary image showing a segmented vessel on a graphical user interface where the vessel region with the first predetermined value is shown as a white area and all other areas are shown as a black area.

5. The method of claim 4, further comprising:
applying a line corresponding to the direction perpendicularly intersecting the longitudinal direction on the binary image,
wherein a portion of the line that overlaps the white area is evaluated in an x-axis direction and a y-axis direction to determine cardiac motion.

6. The method of claim 1, wherein the longitudinal direction of the vessel region is defined by consecutive user inputs being connected with straight lines.

7. The method of claim 1, wherein the longitudinal direction of the vessel region defines a direction in which intravascular image pullback was performed.

8. The method of claim 1, wherein the area is a range of interest.

9. The method of claim 1, further comprising:
estimating a cardiac cycle by evaluating an absolute difference for each angiographic image frame from a first angiographic image frame in the area.

10. The method of claim 1, wherein in the defining, the defined direction perpendicularly intersects the longitudinal direction of the vessel region.

11. The method of claim 1, further comprising:
causing a display unit to display a graphical user interface including an angiography image frame for receiving a user input for co-registration and an item for receiving a user instruction to change the angiography image frame, wherein in the causing, a first angiography image frame during the pullback is displayed.

12. The method of claim 11, wherein the graphical user interface further includes an item to start performing co-registration, and the item is disabled in a case that a number of user inputs in the angiography image frame in the graphical user interface is fewer than a threshold.

13. The method of claim 11, further comprising:
causing the display unit to change from the angiography image frame to a different angiography image frame in the graphical user interface in a case that a number of user inputs in the angiography image is sufficient.

14. The method of claim 11, wherein the graphical user interface further includes a slide bar and a movable cursor along the slide bar, wherein one of the multiple angiography image frames is selected according to a position of the movable cursor, and at least one marker is positioned along the slider bar, at a position corresponding to an angiography image frame selected based on cardiac cycle information.

15. The method of claim 1, further comprising:
causing a display unit to display, while the co-registration is performed, a graphical user interface including an item for receiving a user instruction to stop the co-registration.

16. The method of claim 1, further comprising:
causing a display unit to display, after the co-registration is performed, a graphical user interface including a result of the co-registration, a first item and a second item;
causing the display unit to display, when the first item is selected by a user, a graphical user interface including at least one of the multiple intravascular images, and at least one of the angiography image frames with an indicator indicating the detected marker location; and
causing the display unit to display, when the second item is selected by a user, a graphical user interface including at least one of the multiple intravascular images, and at least one of the angiography image frames without the indicator.

17. The method of claim 1, further comprising:
causing a display unit to display, after the co-registration is performed, a graphical user interface including an indicator indicating a location of the detected marker in the angiography image frame, for receiving a user modification of the location; and
performing co-registration again, based on the received user modification, for at least a part of the multiple intravascular image frames acquired in a certain time range from a time when the angiography image frame is acquired.

18. A non-transitory computer-readable storage medium storing a computer-readable program for causing a computer to execute the method according to claim 1.

19. An imaging apparatus for processing angiography image data, the imaging apparatus comprising:
a memory for storing data;
a processor in communication with the memory for executing the following steps:
detecting a vessel region in each of multiple angiographic image frames;
defining a direction intersecting a longitudinal direction of the vessel region;
detecting motion of the vessel region based on the direction by evaluating positions of the vessel region in the multiple angiographic image frames;
defining an area based on the detected motion and the detected vessel region;
detecting a marker of an imaging catheter disposed in the vessel region within the area; and
performing co-registration based on the detected marker.

20. A method for processing angiographic image data, the method comprising:
detecting a vessel region in multiple angiographic image frames acquired by an imaging catheter in the vessel region during pullback of the imaging catheter;
defining a direction intersecting a longitudinal direction of the vessel region;
detecting motion of the vessel region based on the defined direction by evaluating a position of the vessel region in the multiple angiographic image frames;
defining an area based on the detected motion and the detected vessel region; and
detecting a marker of the imaging catheter disposed in the vessel region within the area, in at least one of the multiple angiography image frames.

* * * * *